United States Patent
Wu

(10) Patent No.: US 11,952,392 B2
(45) Date of Patent: Apr. 9, 2024

(54) ARGINASE INHIBITORS AND METHODS OF USE THEREOF

(71) Applicant: AstraZeneca AB, Sodertalje (SE)

(72) Inventor: Dedong Wu, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 656 days.

(21) Appl. No.: 17/269,569

(22) PCT Filed: Aug. 21, 2019

(86) PCT No.: PCT/EP2019/072341
§ 371 (c)(1),
(2) Date: Feb. 19, 2021

(87) PCT Pub. No.: WO2020/038983
PCT Pub. Date: Feb. 27, 2020

(65) Prior Publication Data
US 2021/0332068 A1    Oct. 28, 2021

Related U.S. Application Data

(60) Provisional application No. 62/721,113, filed on Aug. 22, 2018.

(51) Int. Cl.
*C07F 5/02* (2006.01)

(52) U.S. Cl.
CPC .......... *C07F 5/025* (2013.01); *C07B 2200/13* (2013.01)

(58) Field of Classification Search
CPC ............................. C07F 5/025; C07B 2200/13
See application file for complete search history.

(56) References Cited

U.S. PATENT DOCUMENTS

2016/0375044 A1* 12/2016 Gross ...................... A61P 35/02
514/64

FOREIGN PATENT DOCUMENTS

| JP | 2013525364 A | 6/2013 |
|---|---|---|
| JP | 2018520352 A | 7/2018 |
| JP | 7317841 B2 | 7/2023 |
| WO | 2011133653 A1 | 10/2011 |
| WO | 2016210106 A1 | 12/2016 |
| WO | 2018089490 A1 | 5/2018 |
| WO | 2018119440 A1 | 6/2018 |
| WO | 2019159120 A1 | 8/2019 |
| WO | 2019177873 A1 | 9/2019 |
| WO | 2019205979 A1 | 10/2019 |

OTHER PUBLICATIONS

International Search Report and Written Opinion for International Application No. PCT/EP2019/072341, dated Nov. 7, 2019.

* cited by examiner

*Primary Examiner* — Bahar Craigo
*Assistant Examiner* — Manahil Mirghani Ali Abdalhameed

(57) ABSTRACT

Disclosed include crystalline (S)-2-amino-N-((3R,5R)-8-hydroxy-6-oxo-7-oxa-1-aza-8-boraspiro[4.7]dodecan-3-yl)-3-methylbutanamide in Form D and in Form E:

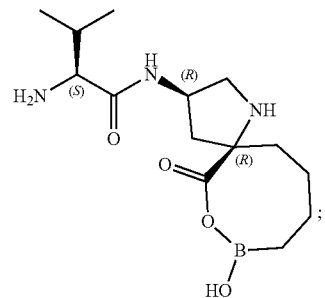

(3R,5R)-8-hydroxy-3-((S)-4-isopropyl-2,2-dimethyl-5-oxo-imidazolidin-1-yl)-7-oxa-1-aza-8-boraspiro[4.7]dodecan-6-one or a pharmaceutically acceptable salt thereof or the crystalline Form 1 thereof:

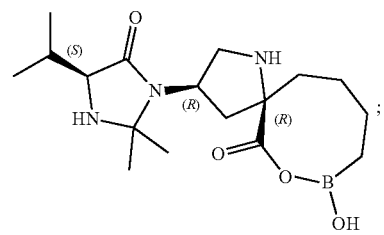

and pharmaceutical compositions and methods of using the same.

27 Claims, 12 Drawing Sheets

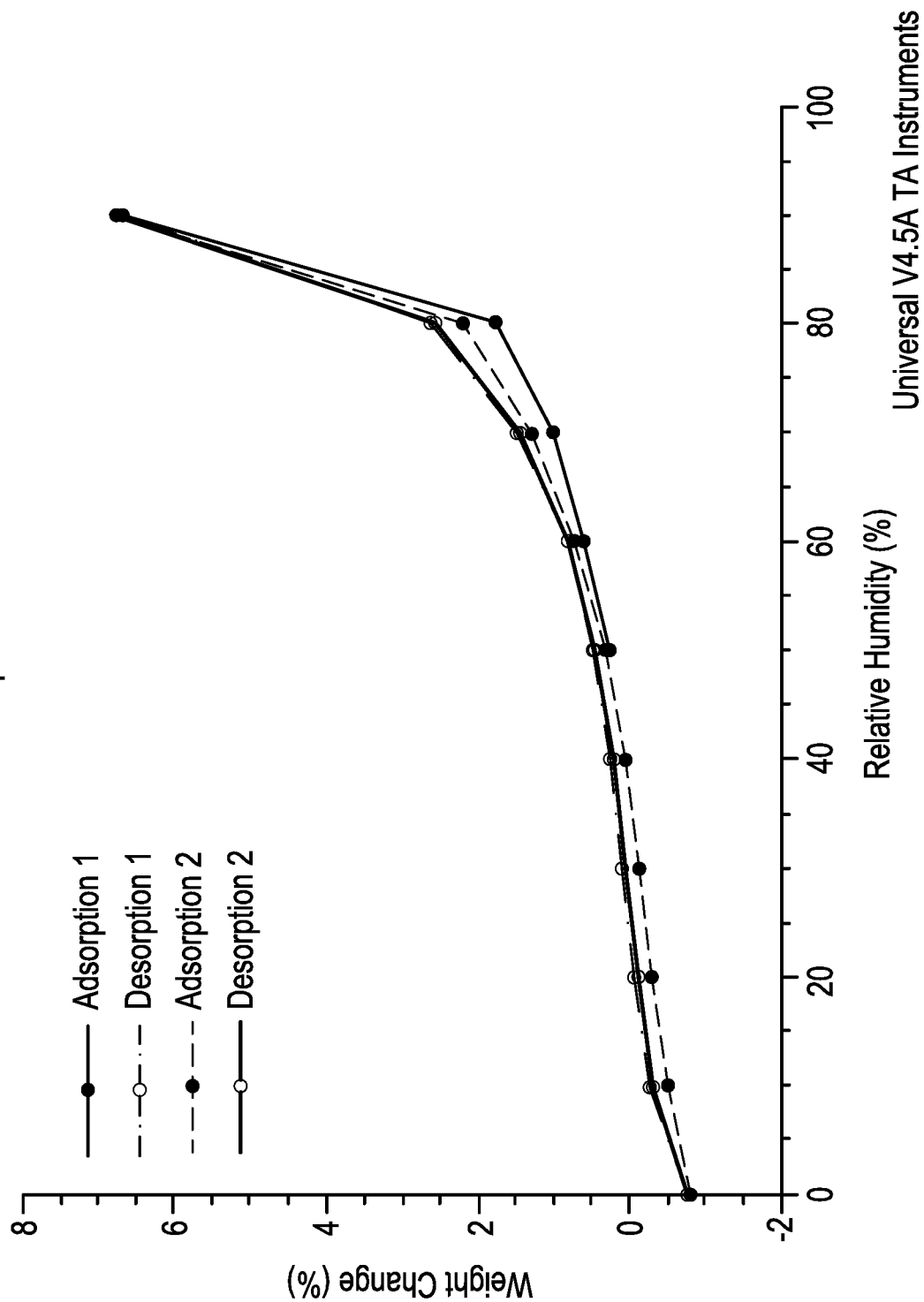

ARGINASE INHIBITORS AND METHODS OF USE THEREOF

CROSS-REFERENCE TO RELATED APPLICATION

This application is a U.S. National Stage application of International Application No. PCT/EP2019/072341, filed on Aug. 21, 2019, which claims the benefit of priority under 35 U.S.C. § 119(e) to U.S. Provisional Application No. 62/721, 113, filed on 22 Aug. 2018 and entitled "Arginase 5 Inhibitors and Methods of Use thereof". Each of the above listed applications is hereby incorporated by reference in its entirety for all purposes.

BACKGROUND

Arginase is a manganese metalloenzyme that catalyzes the conversion of L-arginine to urea and L-ornithine. Two isoforms exist: Arginase 1 is a cytosolic enzyme predominantly found in hepatocytes where it plays a critical role in removing ammonia through urea synthesis, and Arginase 2, a mitochondrial enzyme highly expressed in kidney involved in production of ornithine, a precursor for polyamines and prolines important for cell proliferation and collagen production, respectively.

Although L-arginine is not an essential amino acid as it can be provided through protein turnover in healthy adults, increased expression and secretion of arginases results in reduced L-arginine levels in various physiologic and pathologic conditions (e.g., pregnancy, auto-immune diseases, cancer). Immune cells, in particular, are sensitive to reduced L-arginine levels. T-cells, when faced with a low L-arginine microenvironment, reduce their proliferation rate and lower the expression of CD3ζ chain, IFNγ, and lytic enzymes resulting in impaired T-cell responsiveness. Dendritic cells respond to low L-arginine conditions by reducing their ability to present antigens, and natural killer cells reduce both proliferation and expression of lytic enzymes.

Tumors use multiple immune suppressive mechanisms to evade the immune system. One of these is the reduction of L-arginine through increased levels of circulating arginase, increased expression and secretion of arginase by tumor cells, and recruitment of arginase expressing and secreting myeloid derived suppressor cells. Together, these lead to a reduction of L-arginine in the tumor microenvironment and an immune-suppressive phenotype. Pharmacologic inhibition of arginase activity has been shown to reverse the low L-arginine induced immune suppression in animal models. As such, there is a need for potent and selective arginase inhibitors to reverse immune suppression and re-activate anti-cancer immunity in patients, either as single agent, or in combination with therapies reversing additional immune-suppressive mechanisms.

SUMMARY

In some embodiments, disclosed are crystalline (S)-2-amino-N-((3R,5R)-8-hydroxy-6-oxo-7-oxa-1-aza-8-boraspiro[4.7]dodecan-3-yl)-3-methylbutanamide (chemical structure shown below) in Form D and in Form E:

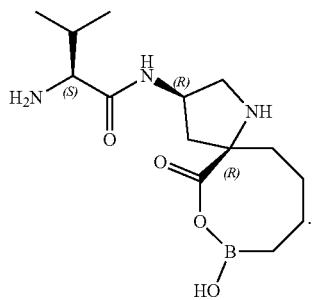

In some embodiments, disclosed is a pharmaceutical composition comprising crystalline (S)-2-amino-N-((3R, 5R)-8-hydroxy-6-oxo-7-oxa-1-aza-8-boraspiro[4.7]dodecan-3-yl)-3-methylbutanamide Form D or Form E, and a pharmaceutically acceptable carrier.

In some embodiments, disclosed is a method of treating cancer comprising administering to a subject in need thereof crystalline (S)-2-amino-N-((3R,5R)-8-hydroxy-6-oxo-7-oxa-1-aza-8-boraspiro[4.7]dodecan-3-yl)-3-methylbutanamide Form D or Form E.

In some embodiments, disclosed is a pharmaceutical composition for treating cancer comprising crystalline (S)-2-amino-N-((3R,5R)-8-hydroxy-6-oxo-7-oxa-1-aza-8-boraspiro[4.7]dodecan-3-yl)-3-methylbutanamide Form D or Form E.

In some embodiments, disclosed is the use of crystalline (S)-2-amino-N-((3R,5R)-8-hydroxy-6-oxo-7-oxa-1-aza-8-boraspiro[4.7]dodecan-3-yl)-3-methylbutanamide Form D or Form E in the manufacture of a medicament for treating cancer.

In some embodiments, disclosed is crystalline (S)-2-amino-N-((3R,5R)-8-hydroxy-6-oxo-7-oxa-1-aza-8-boraspiro[4.7]dodecan-3-yl)-3-methylbutanamide Form D or Form E, for treating cancer.

In some embodiments, disclosed is (3R,5R)-8-hydroxy-3-((S)-4-isopropyl-2,2-dimethyl-5-oxoimidazolidin-1-yl)-7-oxa-1-aza-8-boraspiro[4.7]dodecan-6-one (chemical structure shown below) or a pharmaceutically acceptable salt thereof.

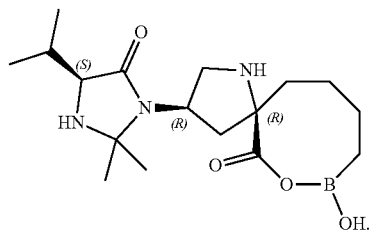

In some embodiments, disclosed is crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one in Form 1.

In some embodiments, disclosed is a pharmaceutical composition comprising (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 and a pharmaceutically acceptable carrier.

In some embodiments, disclosed is a method of treating cancer comprising administering to a subject an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1.

In some embodiments, disclosed is pharmaceutical composition for treating cancer comprising (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1.

In some embodiments, disclosed is (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 for treating cancer.

In some embodiments, disclosed is the use of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 in the manufacture of a medicament for treating cancer.

BRIEF DESCRIPTIONS OF THE DRAWINGS

FIG. 12 illustrates the gravity vapor sorption (GVS) traces of (S)-2-amino-N-((3R,5R)-8-hydroxy-6-oxo-7-oxa-1-aza-8-boraspiro[4.7]dodecan-3-yl)-3-methylbutanamide Form E.

DETAILED DESCRIPTION

Figure 1:
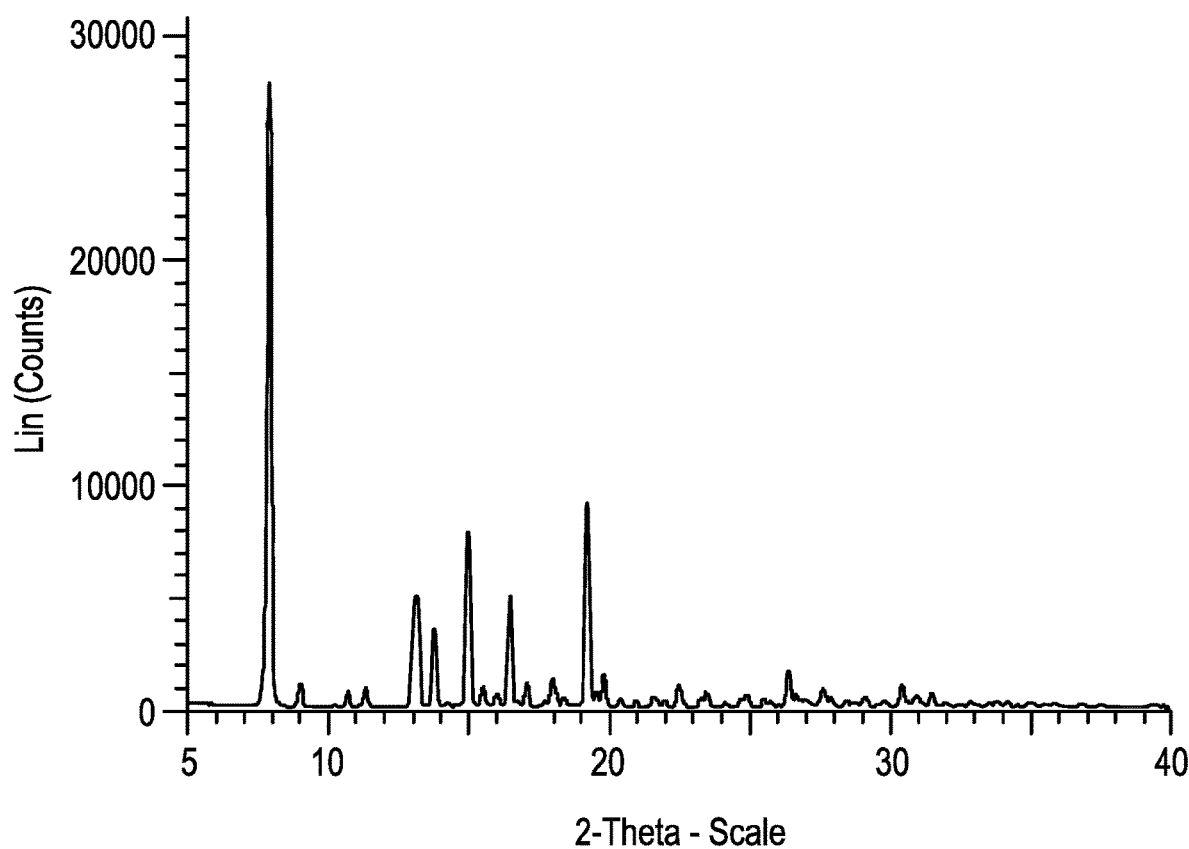
FIG. 1 illustrates the powder X-ray diffraction diagram of (S)-2-amino-N-((3R,5R)-8-hydroxy-6-oxo-7-oxa-1-aza-8-boraspiro[4.7]dodecan-3-yl)-3-methylbutanamide Form D.

In some embodiments, disclosed are crystalline (S)-2-amino-N-((3R,5R)-8-hydroxy-6-oxo-7-oxa-1-aza-8-boraspiro[4.7]dodecan-3-yl)-3-methylbutanamide (chemical structure shown below) in Form D and in Form E:

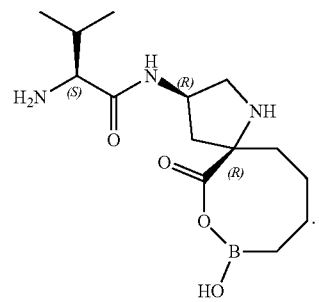

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 7.8°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 19.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 15.0°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 7.8° or at about 19.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 7.8° or at about 15.0°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° at about 15.0° or at about 19.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° selected from about 7.8°, about 19.2° and about 15.0°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern comprising at least one peak expressed as 2θ±0.2° selected from the peaks listed in Table 1. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has an XRPD pattern substantially similar to FIG. 1.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprises peaks with the following 2θ±0.2° values: 7.8, 19.2, and 15.0 degree. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has the X-ray powder diffraction pattern further comprising peaks at 16.4, 13.1, and 13.7 degree 2-theta±0.2°.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprises at least 3 peaks selected from 7.8, 19.2, 15.0, 16.4, 13.1, 13.7, 26.4, 19.8, 17.9, and 22.5 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprises at least 5 peaks selected from 7.8, 19.2, 15.0, 16.4, 13.1, 13.7, 26.4, 19.8, 17.9, and 22.5 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprises at least 7 peaks selected from 7.8, 19.2, 15.0, 16.4, 13.1, 13.7, 26.4, 19.8, 17.9, and 22.5 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprises at least 9 peaks selected from 7.8, 19.2, 15.0, 16.4, 13.1, 13.7, 26.4, 19.8, 17.9, and 22.5 degree 2θ±0.2°.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D is characterized by a differential scanning calorimetry (DSC) curve that comprises an endotherm at about 214° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a DSC thermogram comprising an endotherm of dehydration with an onset at about 213° C. and a peak at about 214° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a DSC thermogram substantially similar to FIG. 3.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a TGA thermogram exhibiting a mass loss of about 0.4% upon heating from about 25° C. to about 150° C. and a mass loss of about 3.1% upon heating from about 150° C. to about 225° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a TGA thermogram substantially similar to FIG. 3.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D absorbs less than about 2% water at the relative humidity (RH) of about 70% and starts to deliquesce after about 80% RH. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a GVS trace substantially similar to FIG. 4.

In some embodiments, disclosed are pharmaceutical compositions comprising an effective amount of crystalline (S)-2-amino-N-((3R,5R)-8-hydroxy-6-oxo-7-oxa-1-aza-8-boraspiro[4.7]dodecan-3-yl)-3-methylbutanamide Form D and a pharmaceutically acceptable carrier. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 85% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 90% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 95% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 96% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 97% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 98% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 99% of (S)-2-amino-N-((3R,5R)-8-hydroxy-6-oxo-7-oxa-1-aza-8-boraspiro[4.7]dodecan-3-yl)-3-methylbutanamide is in Form D. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 99.5% of (S)-2-amino-N-((3R,5R)-8-hydroxy-6-oxo-7-oxa-1-aza-8-boraspiro[4.7]dodecan-3-yl)-3-methylbutanamide is in Form D.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 12.3°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 18.8°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 9.3°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 12.3° or at about 18.8°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 12.3° or at about 9.3°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° at about 18.8° or at about 9.3°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° selected from about 12.3°, about 18.8° and about 9.3°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern comprising at least one peak expressed as 2θ±0.2° selected from the peaks listed in Table 1. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has an XRPD pattern substantially similar to FIG. 9.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprises peaks with the following 2θ±0.2° values: 12.3, 18.8, and 9.3 degree. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has the X-ray powder diffraction pattern further comprising peaks at 14.2, 14.1, and 19.8 degree 2-theta±0.2°.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprises at least 3 peaks selected from 12.3, 18.8, 9.3, 14.2, 14.1, 19.8, 26.2, 17.3, 7.1 and 25.4 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprises at least 5 peaks selected from 12.3, 18.8, 9.3, 14.2, 14.1, 19.8, 26.2, 17.3, 7.1 and 25.4 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprises at least 7 peaks selected from 12.3, 18.8, 9.3, 14.2, 14.1, 19.8, 26.2, 17.3, 7.1 and 25.4 degree 2θ±0.2°. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprises at least 9 peaks selected from 12.3, 18.8, 9.3, 14.2, 14.1, 19.8, 26.2, 17.3, 7.1 and 25.4 degree 2θ±0.2°.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E is characterized by a differential scanning calorimetry (DSC) curve that comprises an endotherm at about 125° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has a DSC thermogram comprising an endotherm of dehydration with an onset at about 105° C. and a peak at about 125° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has a DSC thermogram substantially similar to FIG. 11.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has a TGA thermogram exhibiting a mass loss of about 6.0% upon heating from about 25° C. to about 135° C. and a mass loss of about 3.0% upon heating from about 125° C. to about 225° C. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E has a TGA thermogram substantially similar to FIG. 11.

In some embodiments, crystalline (S)-2-amino-N-((3R,5R)-8-hydroxy-6-oxo-7-oxa-1-aza-8-boraspiro[4.7]dodecan-3-yl)-3-methylbutanamide Form E absorbs less than about 2% water at the relative humidity (RH) of about 80%. In some embodiments, crystalline (S)-2-amino-N-((3R,5R)-8-hydroxy-6-oxo-7-oxa-1-aza-8-boraspiro[4.7]dodecan-3-yl)-3-methylbutanamide Form D has a GVS trace substantially similar to FIG. 12.

In some embodiments, disclosed are pharmaceutical compositions comprising an effective amount of crystalline (S)-2-amino-N-((3R,5R)-8-hydroxy-6-oxo-7-oxa-1-aza-8-boraspiro[4.7]dodecan-3-yl)-3-methylbutanamide Form E and a pharmaceutically acceptable carrier. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 85% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 90% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 95% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 96% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 97% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-

8-hydroxy-6-oxo-7-oxa-1-aza-8-boraspiro[4.7]dodecan-3-yl)-3-methylbutanamide and a pharmaceutically acceptable carrier, wherein at least about 98% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 99% of (S)-2-amino-N-((3R,5R)-8-hydroxy-6-oxo-7-oxa-1-aza-8-boraspiro[4.7]dodecan-3-yl)-3-methylbutanamide is in Form E. In some embodiments, disclosed are pharmaceutical compositions comprising an effective amount of (S)-2-amino-N-((3R,5R)-8-hydroxy-6-oxo-7-oxa-1-aza-8-boraspiro[4.7]dodecan-3-yl)-3-methylbutanamide and a pharmaceutically acceptable carrier, wherein at least about 99.5% of (S)-2-amino-N-((3R,5R)-8-hydroxy-6-oxo-7-oxa-1-aza-8-boraspiro[4.7]dodecan-3-yl)-3-methylbutanamide is in Form E.

In some embodiments, disclosed is compound (3R,5R)-8-hydroxy-3-((S)-4-isopropyl-2,2-dimethyl-5-oxoimidazolidin-1-yl)-7-oxa-1-aza-8-boraspiro[4.7]dodecan-6-one (chemical structure shown below) or a pharmaceutically acceptable salt thereof. The compound can be amorphous, crystalline, or a mixture thereof.

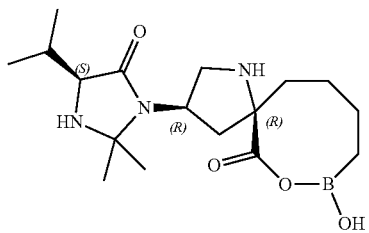

In some embodiments, disclosed is crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1.

In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 11.6°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 8.2°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 13.3°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 11.6° or at about 8.2°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 11.6° or at about 13.3°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° at about 8.2° or at about 13.3°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° selected from about 11.6°, about 8.2° and about 13.3°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern comprising at least one peak expressed as 2θ±0.2° selected from the peaks listed in Table 1. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has an XRPD pattern substantially similar to FIG. 5.

In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 characterized by an X-ray powder diffraction pattern comprises at least 3 peaks selected from 11.6, 8.2, 13.3, 16.4, 12.9, 17.4, 19.5, 16.6, 22.6 and 15.9 degree 2θ±0.2°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 characterized by an X-ray powder diffraction pattern comprises at least 5 peaks selected from 11.6, 8.2, 13.3, 16.4, 12.9, 17.4, 19.5, 16.6, 22.6 and 15.9 degree 2θ±0.2°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 characterized by an X-ray powder diffraction pattern comprises at least 7 peaks selected from 11.6, 8.2, 13.3, 16.4, 12.9, 17.4, 19.5, 16.6, 22.6 and 15.9 degree 2θ±0.2°. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 characterized by an X-ray powder diffraction pattern comprises at least 9 peaks selected from 11.6, 8.2, 13.3, 16.4, 12.9, 17.4, 19.5, 16.6, 22.6 and 15.9 degree 2θ±0.2°.

In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has a DSC thermogram comprising an endotherm of dehydration with an onset at about 82° C. and a peak at about 122° C. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has a DSC thermogram substantially similar to FIG. 7.

In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has a TGA thermogram exhibiting a mass loss of about 5.5% upon heating from about 25° C. to about 150° C. and a mass loss of about 3.2% upon heating from about 150° C. to about 225° C. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one has a TGA thermogram substantially similar to FIG. 7.

In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 absorbs less than about 2% water at the relative humidity (RH) of about 80%. In some embodiments, crystalline (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 has a GVS trace substantially similar to FIG. 8.

In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 and a pharmaceutically acceptable carrier. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7- oxa-1-aza-8-boraspiro[4.7]dodecan-6-one or a pharmaceutically acceptable salt thereof and a pharmaceutically acceptable carrier, wherein at least about 85% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 90% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 95% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 96% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 97% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 98% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 99% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1. In some embodiments, disclosed are pharmaceutical compositions comprising an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one and a pharmaceutically acceptable carrier, wherein at least about 99.5% of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one is in Form 1.

The language "pharmaceutically acceptable carrier" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The amount of active ingredient that is combined with one or more pharmaceutically acceptable carriers to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In one aspect, disclosed are methods for treating cancer in a subject in need thereof, comprising administering to the subject an effective amount (S)-2-amino-N-((3R,5R)-8-hydroxy-6-oxo-7-oxa-1-aza-8-boraspiro[4.7]dodecan-3-yl)-3-methylbutanamide Form D or Form E.

In one aspect, disclosed is (S)-2-amino-N-((3R,5R)-8-hydroxy-6-oxo-7-oxa-1-aza-8-boraspiro[4.7]dodecan-3-yl)-3-methylbutanamide Form D or Form E for use in treating cancer.

In one aspect, disclosed is the use of (S)-2-amino-N-((3R,5R)-8-hydroxy-6-oxo-7-oxa-1-aza-8-boraspiro[4.7]dodecan-3-yl)-3-methylbutanamide Form D or Form E in the manufacture of a medicament for treating cancer.

In one aspect, disclosed is a pharmaceutical compositions comprising (S)-2-amino-N-((3R,5R)-8-hydroxy-6-oxo-7-oxa-1-aza-8-boraspiro[4.7]dodecan-3-yl)-3-methylbutanamide Form D or Form E for use in treating cancer.

In one aspect, disclosed are methods for treating cancer in a subject in need thereof, comprising administering to the subject an effective amount (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1.

In one aspect, disclosed is (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 for use in treating cancer.

In one aspect, disclosed is the use of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 in the manufacture of a medicament for treating cancer.

In one aspect, disclosed is a pharmaceutical compositions comprising (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 for use in treating cancer.

The term "cancer" includes, for example, renal cell carcinoma, head and neck squamous cell carcinoma, lung cancer (e.g., small cell lung cancer (SCLC), non-small cell lung cancer (NSCLC), mesothelioma), pancreatic cancer, colorectal cancer, breast cancer, acute myeloid leukemia (AML), prostate cancer, gastric cancer, bladder cancer, melanoma, renal cancer and ovarian cancer. In some embodiments, the cancer has metastasized. In some embodiments, the cancer is associated with Arginase 1 and/or Arginase 2 modulation.

In some embodiments, the cancer is associated with increased plasma Arginase 1 levels. In some embodiments, the cancer is associated with decreased plasma arginine levels. In some embodiments, the cancer is associated with both increased plasma Arginase 1 levels and decreased plasma arginine levels. In some embodiments, the cancer associated with increased plasma Arginase 1 levels and/or decreased plasma arginine levels includes renal cell carcinoma, head and neck squamous cell carcinoma, lung cancer (e.g., small cell lung cancer (SCLC), non-small cell lung cancer (NSCLC), mesothelioma), pancreatic cancer, colorectal cancer and breast cancer.

In some embodiments, the cancer secretes Arginase 2, for example, acute myeloid leukemia and prostate cancer.

In some embodiments, the cancer is associated with Arginase 1 positive tumor infiltrating immune cells, for example, lung cancer (small cell lung cancer (SCLC), non-small cell lung cancer (NSCLC), gastric cancer, bladder cancer, colorectal cancer, melanoma, head and neck squamous cell carcinoma, breast cancer, prostate cancer, ovarian cancer, pancreatic cancer and renal cancer.

In one aspect, disclosed are methods for inhibiting arginase to a subject in need thereof, comprising administering to the subject an effective amount of (S)-2-amino-N-((3R,5R)-8-hydroxy-6-oxo-7-oxa-1-aza-8-boraspiro[4.7]dodecan-3-yl)-3-methylbutanamide Form D or Form E.

In one aspect, disclosed is (S)-2-amino-N-((3R,5R)-8-hydroxy-6-oxo-7-oxa-1-aza-8-boraspiro[4.7]dodecan-3-yl)-3-methylbutanamide Form D or Form E for use in inhibiting arginase.

In one aspect, disclosed is the use of (S)-2-amino-N-((3R,5R)-8-hydroxy-6-oxo-7-oxa-1-aza-8-boraspiro[4.7]dodecan-3-yl)-3-methylbutanamide Form D or Form E in the manufacture of a medicament for inhibiting arginase.

In one aspect, disclosed are pharmaceutical compositions comprising (S)-2-amino-N-((3R,5R)-8-hydroxy-6-oxo-7-oxa-1-aza-8-boraspiro[4.7]dodecan-3-yl)-3-methylbutanamide Form D or Form E for use in inhibiting arginase.

In one aspect, disclosed are methods for inhibiting arginase to a subject in need thereof, comprising administering to the subject an effective amount of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or the crystalline Form 1.

In one aspect, disclosed is (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 for use in inhibiting arginase.

In one aspect, disclosed is the use of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 in the manufacture of a medicament for inhibiting arginase.

In one aspect, disclosed are pharmaceutical compositions comprising (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 for use in inhibiting arginase.

The term "arginase" includes manganese-containing enzymes belonging to the ureahydrolase family that catalyze the fifth and final step in the urea cycle converting L-arginine into L-ornithine and urea. The term "arginase" includes the two isozymes of the enzyme, e.g., Arginase 1, which functions in the urea cycle, and is located primarily in the cytoplasm of the liver, and Arginase 2, which is located in the mitochondria of several tissues in the body and is implicated in the regulation of arginine/ornithine concentrations in the cell. In some embodiments, (S)-2-amino-N-((3R,5R)-8-hydroxy-6-oxo-7-oxa-1-aza-8-boraspiro[4.7]dodecan-3-yl)-3-methylbutanamide Form D or Form E is selective for Arginase 1. In some embodiments, (S)-2-amino-N-((3R,5R)-8-hydroxy-6-oxo-7-oxa-1-aza-8-boraspiro[4.7]dodecan-3-yl)-3-methylbutanamide Form D or Form E is selective for Arginase 2. In some embodiments, (S)-2-amino-N-((3R,5R)-8-hydroxy-6-oxo-7-oxa-1-aza-8-boraspiro[4.7]dodecan-3-yl)-3-methylbutanamide Form D or Form E inhibit both Arginase 1 and Arginase 2. In some embodiments, (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 is selective for Arginase 1. In some embodiments, (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 is selective for Arginase 2. In some embodiments, (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 inhibit both Arginase 1 and Arginase 2.

The language "effective amount" includes an amount of (S)-2-amino-N-((3R,5R)-8-hydroxy-6-oxo-7-oxa-1-aza-8-boraspiro[4.7]dodecan-3-yl)-3-methylbutanamide Form D or Form E or (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1, that will elicit a biological or medical response in a subject, for example, the reduction or inhibition of enzyme or protein activity related to arginase or cancer, amelioration of symptoms of cancer or the slowing or delaying of progression of cancer. In some embodiments, the language "effective amount" includes the amount of (S)-2-amino-N-((3R,5R)-8-hydroxy-6-oxo-7-oxa-1-aza-8-boraspiro[4.7]dodecan-3-yl)-3-methylbutanamide Form D or Form E or (3R,5R)-8-hydroxy-3-((S)-4-isopropyl-2,2-dimethyl-5-oxoimidazolidin-1-yl)-7-oxa-1-aza-8-boraspiro[4.7]dodecan-6-one or a pharmaceutically acceptable salt thereof or the crystalline Form 1 that when administered to a subject, is effective to at least partially alleviate, inhibit, and/or ameliorate cancer or inhibit arginase, and/or reduce or inhibit the growth of a tumor or proliferation of cancerous cells in a subject.

The term "subject" includes warm blooded mammals, for example, primates, dogs, cats, rabbits, rats, and mice. In some embodiments, the subject is a primate, for example, a human. In some embodiments, the subject is suffering from cancer. In some embodiments, the subject is in need of treatment (e.g., the subject would benefit biologically or medically from treatment). In some embodiments, the patient is suffering from cancer. In some embodiments, the subject has increased plasma Arginase 1 levels. In some embodiments, the subject has decreased arginine levels. In some embodiments, the patient has both increased plasma Arginase 1 levels and decreased arginine levels. In some embodiments, the subject has a cancer secreting Arginase 2 (e.g., acute myeloid leukemia or prostate cancer). In some embodiments, the subject has Arginase 1 positive tumor infiltrating immune cells.

The language "inhibit," "inhibition" or "inhibiting" includes a decrease in the baseline activity of a biological activity or process The language "treat," "treating" and "treatment" includes the reduction or inhibition of enzyme or protein activity related to arginase or in a subject, amelioration of one or more symptoms of a cancer, or the slowing or delaying of progression of cancer in a subject. The language "treat," "treating" and "treatment" also includes the reduction or inhibition of the growth of a tumor or proliferation of cancerous cells in a subject.

In some embodiments, the present compounds, e.g., (S)-2-amino-N-((3R,5R)-8-hydroxy-6-oxo-7-oxa-1-aza-8-boraspiro[4.7]dodecan-3-yl)-3-methylbutanamide and (3R,5R)-8-hydroxy-3-((S)-4-isopropyl-2,2-dimethyl-5-oxoimidazolidin-1-yl)-7-oxa-1-aza-8-boraspiro[4.7]dodecan-6-one, show interconversion of structures between a free boronic acid and a boronate ester, as illustrated in Scheme 1 below.

Scheme 1. Interconversion of the Free Boronic Acid and Boronate Ester of Form D.

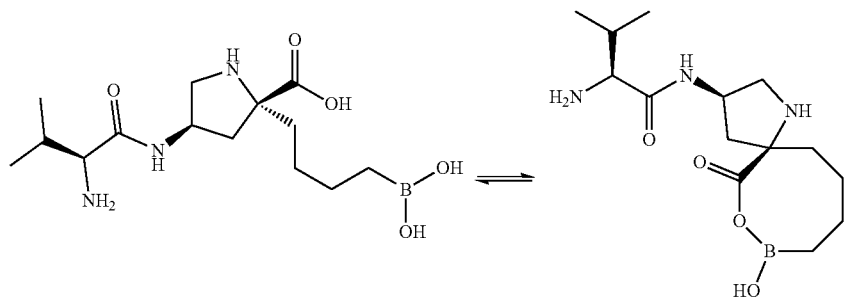 [SMILES: CC(C)[C@H](N)C(=O)N[C@H]1CN[C@@](CCCCB(O)O)(C(=O)O)C1 ; CC(C)[C@H](N)C(=O)N[C@H]1CN[C@]2(CCCCB(O)OC2=O)C1]

In some embodiments, the present compounds, e.g., (S)-2-amino-N-((3R,5R)-8-hydroxy-6-oxo-7-oxa-1-aza-8-boraspiro[4.7]dodecan-3-yl)-3-methylbutanamide and (3R,5R)-8-hydroxy-3-((S)-4-isopropyl-2,2-dimethyl-5-oxoimidazolidin-1-yl)-7-oxa-1-aza-8-boraspiro[4.7]dodecan-6-one, can be in a form where a dative bond is formed between the nitrogen atom of the pyrrolidine moiety and the boron atom. In the formation of a conventional covalent bond, each atom supplies one electron to the bond, while in a dative bond (also known as coordinate bond), both electrons come from the same atom. For example, the dative bond between the nitrogen and boron atoms in the present compound is formed by sharing the pair of electrons from the nitrogen atom. The dative bond in (S)-2-amino-N-((3R,5R)-8-hydroxy-6-oxo-7-oxa-1-aza-8-boraspiro[4.7]dodecan-3-yl)-3-methylbutanamide and (3R,5R)-8-hydroxy-3-((S)-4-isopropyl-2,2-dimethyl-5-oxoimidazolidin-1-yl)-7-oxa-1-aza-8-boraspiro[4.7]dodecan-6-one, can be represented by an arrowed line in the following structural formula, respectively:

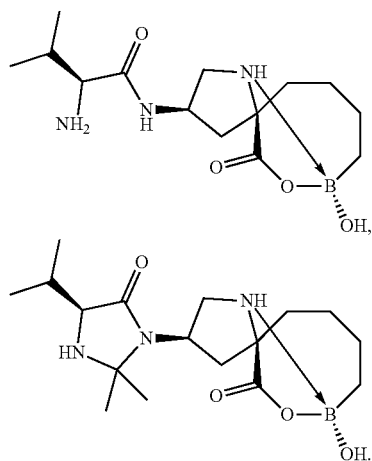

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) preparative chromatography was performed on a Gilson prep HPLC instrument with UV collection; alternatively, preparative chromatography was performed on a Waters AutoPurification HPLC-MS instrument with MS- and UV-triggered collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection; alternatively, chiral preparative chromatography was performed on a Waters Prep 100 SFC-MS instrument with MS- and UV-triggered collection or a Thar MultiGram III SFC instrument with UV collection.

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal.

(viii) in general, end-products of the Formula I were also characterized by mass spectroscopy following liquid chromatography (LCMS or UPLC); UPLC was carried out using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm), for basic analysis the column used was a Waters Acquity BEH C18 (1.7 μm 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 mins (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 μm, 2.1×30 mm), for basic analysis the column used was a Waters Acquity BEH C18 (1.7 μm, 2.1×30 mm); LCMS was carried out using a Waters Alliance HT (2795) fitted with a Waters ZQ ESCi mass spectrometer and a Phenomenex Gemini-NX C18 (5 μm, 110 A, 2.1×50 mm column at a flow rate of 1.1 mL/min 95% A to 95% B over 4 min with a 0.5 min hold where A=0.1% formic acid and B=0.1% formic acid in acetonitrile (for acidic work) or A=0.1% ammonium hydroxide in water and B=acetonitrile (for basic work). Additionally, LCMS was carried out using a Shimadzu UFLC fitted with a Shimadzu LCMS-2020 mass spectrometer and a Waters HSS C18 (1.8 μm, 2.1×50 mm) or Shim-pack XR-ODS (2.2 μm, 3.0×50 mm) or Phenomenex Gemini-NX C18 (3 μm, 3.0×50 mm) column at a flow rate of 0.7 mL/min (for Waters HSS C18 column), 1.0 mL/min (for Shim-pack XR-ODS column) or 1.2 mL/min (for Phenomenex Gemini-NX C18), 95% A to 95% B over 2.2 min with a 0.6 min hold, where A=0.1% formic acid or 0.05% trifluoroacetic acid in water (for acidic work) or 0.1% ammonium hydroxide or 6.5 mM ammonium carbonate in water (for basic work) andB=acetonitrile. The reported molecular ion corresponds to the [M+H]+ unless otherwise specified; for molecules with multiple isotopic patterns (Br, Cl, etc.) the reported value is the one obtained for the lowest isotope mass unless otherwise specified.

(ix) ion exchange purification was generally performed using an SCX-2 (Biotage) cartridge.

(x) intermediate purity was assessed by thin layer chromatographic, mass spectroscopy, LCMS, UPLC/MS, HPLC (high performance liquid chromatography) and/or NMR analysis;

(xi) the following abbreviations have been used:—
EtOAc: ethyl acetate
DMSO: dimethylsulfoxide
KHMDS: potassium hexamethyldisilazane
MeOH: methanol
MeCN: acetonitrile
LCMS: liquid chromatography-mass spectrometry
rt or RT: room temperature
aq: aqueous
THF: tetrahydrofuran
DCM: dichloromethane
DMF: dimethylformamide
HATU: (1-[Bis(dimethylamino)methylene]-1H-1,2,3-triazolo[4,5-b]pyridinium 3-oxid hexafluorophosphate)
HEPES: (4-(2-hydroxyethyl)-1-piperazineethanesulfonic acid)
XRPD X-ray powder diffraction
DSC differential scanning calorimetry
TGA thermogravimetric analysis
GVS gravity vapor sorption Example 1: Synthesis of (S)-2-amino-N-((3R,5R)-8-hydroxy-6-oxo-7-oxa-1-aza-8-boraspiro[4.7]dodecan-3-yl)-3-methylbutanamide Form D Intermediate 1: (2S,4R)-1-tert-butyl 2-methyl 4-azidopyrrolidine-1,2-dicarboxylate

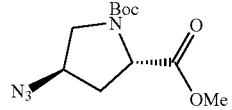 [SMILES: COC(=O)[C@@H]1C[C@@H](N=[N+]=[N-])CN1C(=O)OC(C)(C)C]

Methanesulfonyl chloride (2.86 mL, 36.7 mmol) was added dropwise to a solution of (2S,4S)-1-tert-butyl 2-methyl 4-hydroxypyrrolidine-1,2-dicarboxylate (7.50 g, 30.6 mmol) and triethylamine (5.11 mL, 36.7 mmol) in DCM (38 mL) at 0° C. The reaction mixture stirred at 0° C. for 1 h before warming to room temperature with stirring for an additional 1 h. The reaction mixture was diluted with dichloromethane and washed with water. The organic layer was dried over $Na_2SO_4$, filtered and concentrated to dryness to afford 1-(tert-butyl) 2-methyl (2S,4S)-4-((methylsulfonyl)oxy)pyrrolidine-1,2-dicarboxylate (9.9 g, 100% yield) which was used without further purification. m/z (ES$^+$) [M+NH$_4$]$^+$=341.

Sodium azide (5.96 g, 91.7 mmol) was added to a solution of 1-(tert-butyl) 2-methyl (2S,4S)-4-((methylsulfonyl)oxy) pyrrolidine-1,2-dicarboxylate (9.89 g, 30.6 mmol) in DMF (30 mL). The reaction mixture was heated to 50° C. and stirred overnight. The reaction mixture was cooled to room temperature and concentrated. The resulting residue was diluted with EtOAc and washed with water. The organic layer was dried over $Na_2SO_4$, filtered and concentrated to dryness. Crude material was purified by silica gel chromatography (hexanes/EtOAc) to afford the product (Intermediate 1, 5.95 g, 72% yield) as a mixture of rotamers. $^1$H NMR (300 MHz, DMSO-d$_6$) δ 1.33 and 1.40 (9H, s ×2) rotamers, 2.08-2.22 (1H, m), 2.26-2.41 (1H, m), 3.41 (1H, dt), 3.48-3.61 (1H, m), 3.65 and 3.68 (3H, s ×2) rotamers, 4.22 (1H, dd), 4.30-4.43 (1H, m); m/z (ES$^+$) [M+H]$^+$=271.

Intermediate 2: (2S,4R)-2-benzyl 1-tert-butyl 4-azidopyrrolidine-1,2-dicarboxylate

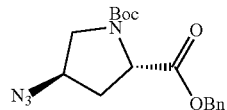 [SMILES: CC(C)(C)OC(=O)N1C[C@H](N=[N+]=[N-])C[C@H]1C(=O)OCc1ccccc1]

A solution of sodium hydroxide (5.28 g, 132 mmol) in water (22 mL) was added dropwise to a solution of (2S, 4R)-1-tert-butyl 2-methyl 4-azidopyrrolidine-1,2-dicarboxylate (Intermediate 1, 5.95 g, 22.0 mmol) in THF (44 mL) and MeOH (22 mL) at 0° C. The reaction mixture was stirred overnight while slowly warming to room temperature. The volatiles were removed in vacuo and the aqueous layer was acidified to pH ~3 with 5 M HCl and extracted with DCM. The combined organics were dried over $Na_2SO_4$, filtered and concentrated to dryness to afford (2S,4R)-4-azido-1-(tert-butoxycarbonyl)pyrrolidine-2-carboxylic acid (5.64 g, 100% yield) as a mixture of rotamers which was used without further purification. $^1$H NMR (300 MHz, DMSO-d$^6$) δ 1.35 and 1.40 (9H, s ×2) rotamers, 2.07-2.18 (1H, m), 2.26-2.38 (1H, m), 3.34-3.44 (1H, m), 3.48-3.63 (1H, m), 4.09-4.17 (1H, m), 4.30-4.37 (1H, m); m/z (ES$^-$) [M+HCOO]$^-$=301.

Benzyl bromide (2.83 mL, 23.8 mmol) was added dropwise to a solution of (2S,4R)-4-azido-1-(tert-butoxycarbonyl)pyrrolidine-2-carboxylic acid (5.19 g, 19.9 mmol) and triethylamine (3.46 mL, 24.8 mmol) in DMF (60 mL) and the reaction mixture stirred overnight at room temperature. The volatiles were removed in vacuo and the resulting residue was dissolved in EtOAc and washed with water. The organic layer was dried over Na$_2$SO$_4$, filtered and concentrated to dryness. Crude material was purified by silica gel chromatography (hexanes/EtOAc) to afford the product (Intermediate 2, 5.09 g, 74% yield). $^1$H NMR (300 MHz, DMSO-d$_6$) δ 1.26 and 1.39 (9H, s ×2) rotamers, 2.11-2.23 (1H, m), 2.31-2.43 (1H, m), 3.43 (1H, ddd), 3.50-3.59 (1H, m), 4.25-4.40 (2H, m), 5.07-5.22 (2H, m), 7.31-7.40 (5H, m); m/z (ES$^+$) [M+H]$^+$=347.

Intermediate 3: (4R)-2-benzyl 1-tert-butyl 4-azido-2-(but-2-enyl)pyrrolidine-1,2-dicarboxylate

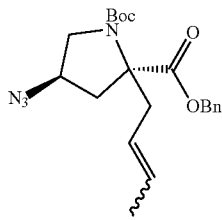

(2S,4R)-2-benzyl 1-tert-butyl 4-azidopyrrolidine-1,2-dicarboxylate (Intermediate 2, 5.09 g, 14.7 mmol) and crotyl bromide (2.27 mL, 22.0 mmol) were dissolved in THF (100 mL) and the solution was cooled to −78° C. under an atmosphere of N$_2$. The solution was treated with dropwise addition of a solution of KHMDS (0.5M in toluene, 44.1 mL, 22.0 mmol). The reaction mixture was slowly warmed to room temperature and stirred for 3 h. The crude reaction mixture was quenched with water and the volatiles were removed in vacuo. The crude mixture was diluted in DCM and the layers were separated. The organic layer was washed with water, dried over Na$_2$SO$_4$, filtered and concentrated to dryness. The crude material was purified by silica gel chromatography (hexanes/EtOAc) to afford the product (Intermediate 3, 4.6 g, 78% yield) as a mixture of rotamers and E/Z olefins. $^1$H NMR (300 MHz, DMSO-d$_6$) δ 1.26-1.43 (9H, m), 1.59-1.66 (3H, m), 2.07-2.17 (1H, m), 2.32-2.48 (2H, m), 2.57-3.12 (2H, m), 3.35-3.82 (1H, m), 4.20-4.38 (1H, m), 5.02-5.22 (2H, m), 5.24-5.41 (1H, m), 5.46-5.68 (1H, m), 7.28-7.42 (5H, m); m/z (ES$^+$) [M+H]$^+$=401.

Intermediate 4: (4R)-2-benzyl 1-tert-butyl 4-azido-2-(4-(4,4,5,5-tetramethyl-1,3,2-dioxaborolan-2-yl)butyl)pyrrolidine-1,2-dicarboxylate

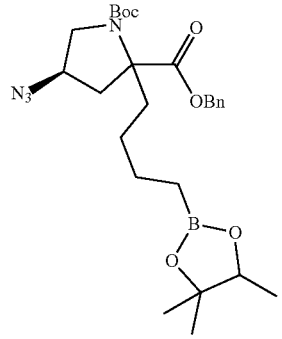 [SMILES: CC1OB(CCCCC2(C(=O)OCc3ccccc3)C[C@@H](N=[N+]=[N-])CN2C(=O)OC(C)(C)C)OC1(C)C]

Bis(1,5-cyclooctadiene)diiridium(I) dichloride (772 mg, 1.15 mmol) and bis(diphenylphosphino)methane (883 mg, 2.30 mmol) were added to an oven-dried round-bottom flask. The flask was sealed and purged with N$_2$. The solids were dissolved in DCM (66 mL) and 4,4,5,5-tetramethyl-1,3,2-dioxaborolane (3.67 mL, 25.3 mmol) was slowly added to the solution. The reaction stirred at room temperature for 10 min. (4R)-2-benzyl 1-tert-butyl 4-azido-2-(but-2-enyl)pyrrolidine-1,2-dicarboxylate (Intermediate 3, 4.60 g, 11.5 mmol) was added to the reaction as a solution in DCM (44 mL) and the reaction mixture stirred overnight. The reaction mixture was diluted with DCM and quenched with water. The layers were separated and the aqueous layer was extracted with DCM. The combined organics were dried over Na$_2$SO$_4$, filtered and concentrated to dryness. The crude material was purified by silica gel chromatography (hexanes/EtOAc) to afford (4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 4, 2.7 g, 44% yield).

Intermediate 5: (2S,4R)-2-benzyl 1-tert-butyl 4-azido-2-(4-(4,4,5,5-tetramethyl-1,3,2-dioxaborolan-2-yl)butyl)pyrrolidine-1,2-dicarboxylate and Intermediate 6: (2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate

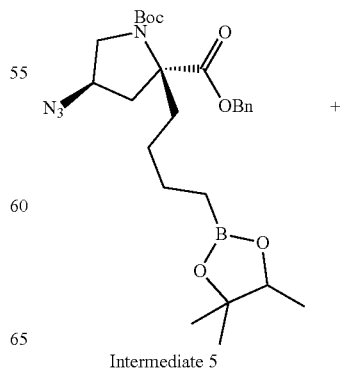

Intermediate 5

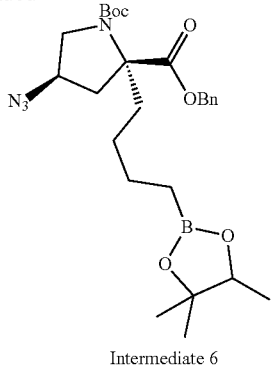

Intermediate 6

The purified material obtained from the synthesis of Intermediate 4 was subjected to chiral SFC (Chiralpak IG column, 21.2×250 mm, 5 μm, Temperature=23° C., Mobile phase=0-7% MeOH (w/0.2% NH$_4$OH):CO$_2$, UV detection @ 220 nm, loading=16.8 mg/inj, conc=112.5 ng/mL in MeOH, flow rate=70 mL/min, Outlet Pressure=100 bar] to give two diastereomers. The stereochemistry for the major diastereomer Intermediate 6 was assigned as the anti-addition product and the minor diastereomer Intermediate 5 the syn-addition product.

Intermediate 5 (436 mg): (2S,4R)-2-benzyl 1-tert-butyl 4-azido-2-(4-(4,4,5,5-tetramethyl-1,3,2-dioxaborolan-2-yl)butyl)pyrrolidine-1,2-dicarboxylate. $^1$H NMR (400 MHz, DMSO-d$_6$) δ 0.58-0.70 (2H, m), 1.17 (12H, s), 1.25-1.40 (13H, m), 1.74-1.83 (1H, s), 2.00-2.11 (2H, m), 2.38-2.47 (1H, m), 3.07-3.16 (1H, m), 3.81 (1H, m), 4.29-4.34 (1H, m), 5.04-5.17 (2H, m), 7.34-7.39 (m, 5H); m/z (ES$^+$) [M+H]$^+$=529.

Intermediate 6 (1.60 g): (2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate. $^1$H NMR (400 MHz, DMSO-d$_6$) δ 0.56-0.73 (2H, m), 0.98-1.13 (1H, m), 1.17 (12H, s), 1.26-1.37 (13H, m), 1.66-1.79 (1H, m), 2.01-2.22 (2H, m), 2.34-2.47 (1H, m), 3.60 (1H, br dd), 4.29-4.35 (1H, m), 5.04-5.18 (2H, m), 7.31-7.40 (5H, m); m/z (ES$^+$) [M+H]$^+$=529.

Intermediate 7: (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate

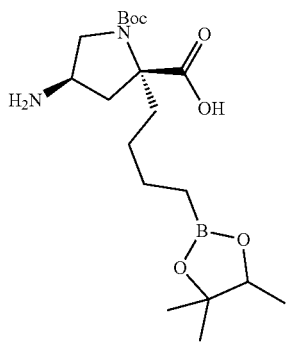 [SMILES: CC1OB(CCCC[C@]2(C(=O)O)C[C@@H](N)CN2C(=O)OC(C)(C)C)OC1(C)C]

(2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 6, 688 mg, 1.30 mmol) was dissolved in ethyl acetate (13 mL) and methanol (4 mL) and treated with Pd/C (10% wt, 346 mg, 0.325 mmol). The flask was equipped with a balloon of H$_2$ and the suspension stirred overnight at room temperature. The reaction mixture was filtered through diatomaceous earth and rinsed with methanol. The filtrate was concentrated under reduced pressure to afford the product (Intermediate 7, 500 mg, 93% yield) which was used without further purification. $^1$H NMR (300 MHz, DMSO-d$_6$) δ 0.67 (2H, t), 0.94-1.00 (1H, m), 1.17 (12H, s), 1.22-1.38 (11H, m), 1.43-1.53 (1H, m), 1.85 (1H, d), 2.00-2.15 (2H, m), 3.23 (2H, dd), 3.58-3.61 (1H, m), 3.80-3.88 (1H, m), 8.96 (2H, m); m/z (ES$^+$) [M+H]$^+$=413.

Intermediate 8: (2R,4R)-2-benzyl 1-tert-butyl 4-((R)-2-(tert-butoxycarbonylamino)-3-methylbutanamido)-2-(4-(4,4,5,5-tetramethyl-1,3,2-dioxaborolan-2-yl)butyl)pyrrolidine-1,2-dicarboxylate

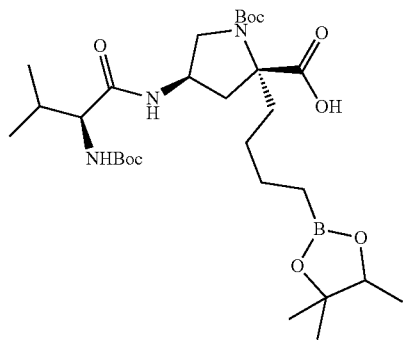 [SMILES: CC(C)[C@H](NC(=O)OC(C)(C)C)C(=O)N[C@H]1CN(C(=O)OC(C)(C)C)[C@@](CCCCB2OC(C)C(C)(C)O2)(C(=O)O)C1]

Triethylamine (0.21 mL, 1.5 mmol) and HATU (254 mg, 0.668 mmol) were added sequentially to a solution of Boc-Val-OH (145 mg, 0.668 mmol) in DMF (2.9 mL) and the reaction was stirred at room temperature for 30 min. (2R,4R)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 7, 250 mg, 0.606 mmol) was added to the reaction mixture as a solution in DMF (2.9 mL). The reaction stirred at room temperature overnight. The crude reaction mixture was concentrated and directly purified by silica gel chromatography (hexanes/EtOAc) to afford the product (Intermediate 8, 250 mg, 67% yield) as a mixture of rotamers. $^1$H NMR (300 MHz, DMSO-d$_6$) δ 0.64-0.73 (2H, m), 0.73-0.85 (6H, m), 1.13-1.14 (1H, m), 1.17 (12H, s), 1.22-1.42 (22H, m), 1.56-1.75 (1H, m), 1.79-1.97 (1H, m), 2.00-2.26 (2H, m), 3.08-3.24 (1H, m), 3.54-3.77 (2H, m), 4.12-4.36 (1H, m), 6.58 (1H, t), 7.96-8.03 (2H, m); m/z (ES$^+$) [M+H]$^+$=584.

Intermediate 9: (2R,4R)-4-((S)-2-amino-3-methylbutanamido)-2-(4-boronobutyl)pyrrolidine-2-carboxylic Acid

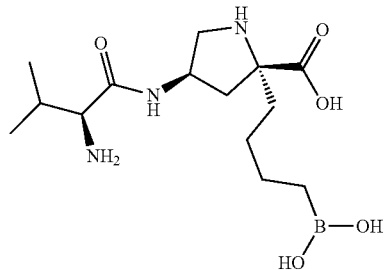 [SMILES: CC(C)[C@H](N)C(=O)N[C@H]1CN[C@@](CCCCB(O)O)(C(=O)O)C1]

Trifluoroacetic acid (0.63 mL, 8.2 mmol) was added to a solution (2R,4R)-1-(tert-butoxycarbonyl)-4-((S)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid (Intermediate 8, 250 mg, 0.409 mmol) in DCM (4 mL). The resulting solution stirred at room temperature for 1 h and was then concentrated under vacuum. The crude amino acid was dissolved in $Et_2O$ (2 mL) and 1 M aq HCl (2 mL). Phenylboronic acid (99 mg, 0.81 mmol) was added and the clear biphasic solution stirred at room temperature for 1 h. The reaction mixture was diluted with water and washed with $Et_2O$. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% acetonitrile in water) to afford (2R,4R)-4-((S)-2-amino-3-methylbutanamido)-2-(4-boronobutyl)pyrrolidine-2-carboxylic acid (Intermediate 9, 28 mg, 20% yield) as a white solid and a mixture of rotamers. $^1H$ NMR (300 MHz, $D_2O$) δ 0.66-0.76 (2H, m), 0.85 (6H, dd), 1.07-1.43 (4H, m), 1.55-1.68 (1H, m), 1.77-1.97 (2H, m), 2.13-2.33 (2H, m), 3.07 (1H, d), 3.08-3.16 (1H, m), 3.37-3.48 (1H, m), 4.27-4.40 (1H, m); m/z $(ES^+)$ $[M+H]^+=330$.

Example 1: (S)-2-amino-N-((3R,5R)-8-hydroxy-6-oxo-7-oxa-1-aza-8-boraspiro[4.7]dodecan-3-yl)-3-methylbutanamide Form D

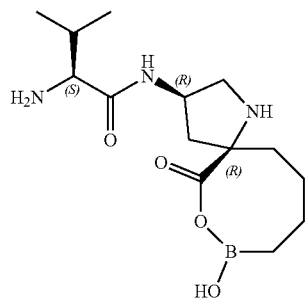

An amount of 20.5 mg of Intermediate 9 was suspended in 0.50 mL of MeCN. The suspension was heated to 75° C. and stirred at 75° C. for 1 hour. The suspension was then cooled down to the ambient temperature and the solid was filtered and dried in air. Crystalline material with needle/rod crystals was obtained and designated as (S)-2-amino-N-((3R,5R)-8-hydroxy-6-oxo-7-oxa-1-aza-8-boraspiro[4.7]dodecan-3-yl)-3-methylbutanamide Form D.

Example 1 was analyzed by XRPD and the results are tabulated below (Table 1) and shown in FIG. 1.

TABLE 1

| XRPD Peaks for Form D ||
| Angle (2θ ± 0.2°) | Intensity (%) |
| --- | --- |
| 7.8 | 100.0 |
| 19.2 | 33.1 |
| 15.0 | 27.7 |
| 16.4 | 18.0 |
| 13.1 | 18.0 |
| 13.7 | 12.5 |
| 26.4 | 6.0 |
| 19.8 | 5.6 |
| 17.9 | 4.9 |
| 22.5 | 4.1 |

Example 1 was characterized in providing at least one of the following 2θ±0.2° values measured using CuKα radiation: 7.8, 19.2, and 15.0°.

Single crystals of Example 1 were obtained from slow evaporation of an acetonitrile solution and single crystal structure analysis confirmed that Example 1 is an anhydrous form.

Figure 2:
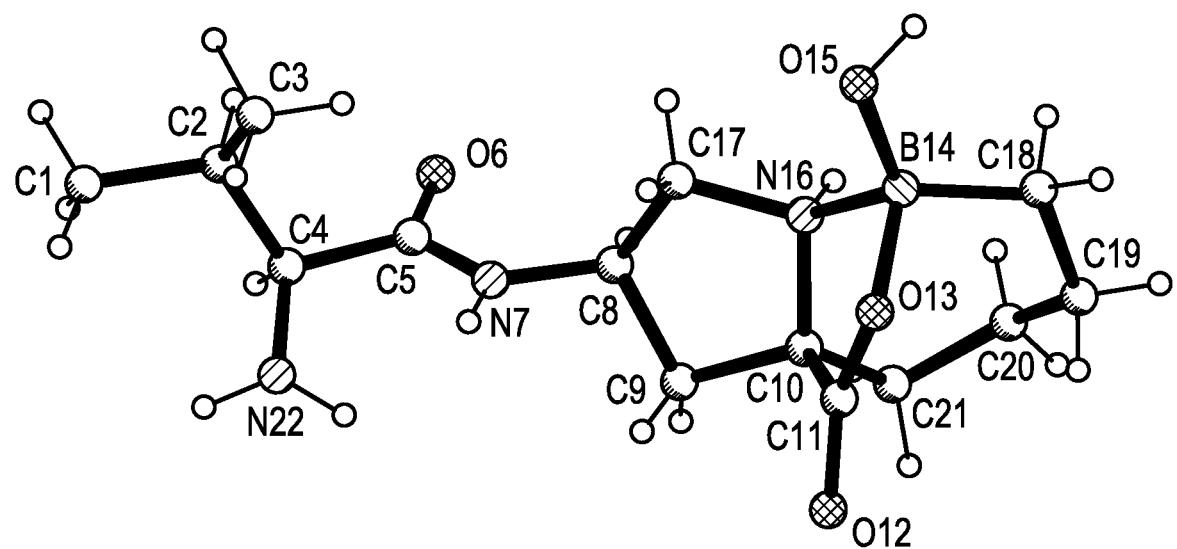
FIG. 2 illustrates the single crystal structure of (S)-2-amino-N-((3R,5R)-8-hydroxy-6-oxo-7-oxa-1-aza-8-boraspiro[4.7]dodecan-3-yl)-3-methylbutanamide Form D.

The molecular structure of Example 1 is shown in FIG. 2. Crystallographic data: Space group orthorhombic $P2_12_12_1$, unit cell dimensions: a=10.9250(6) Å, b=12.9532(8) Å, c=23.8051(14) Å, V=3368.7(3) Å$^3$.

Figure 3:
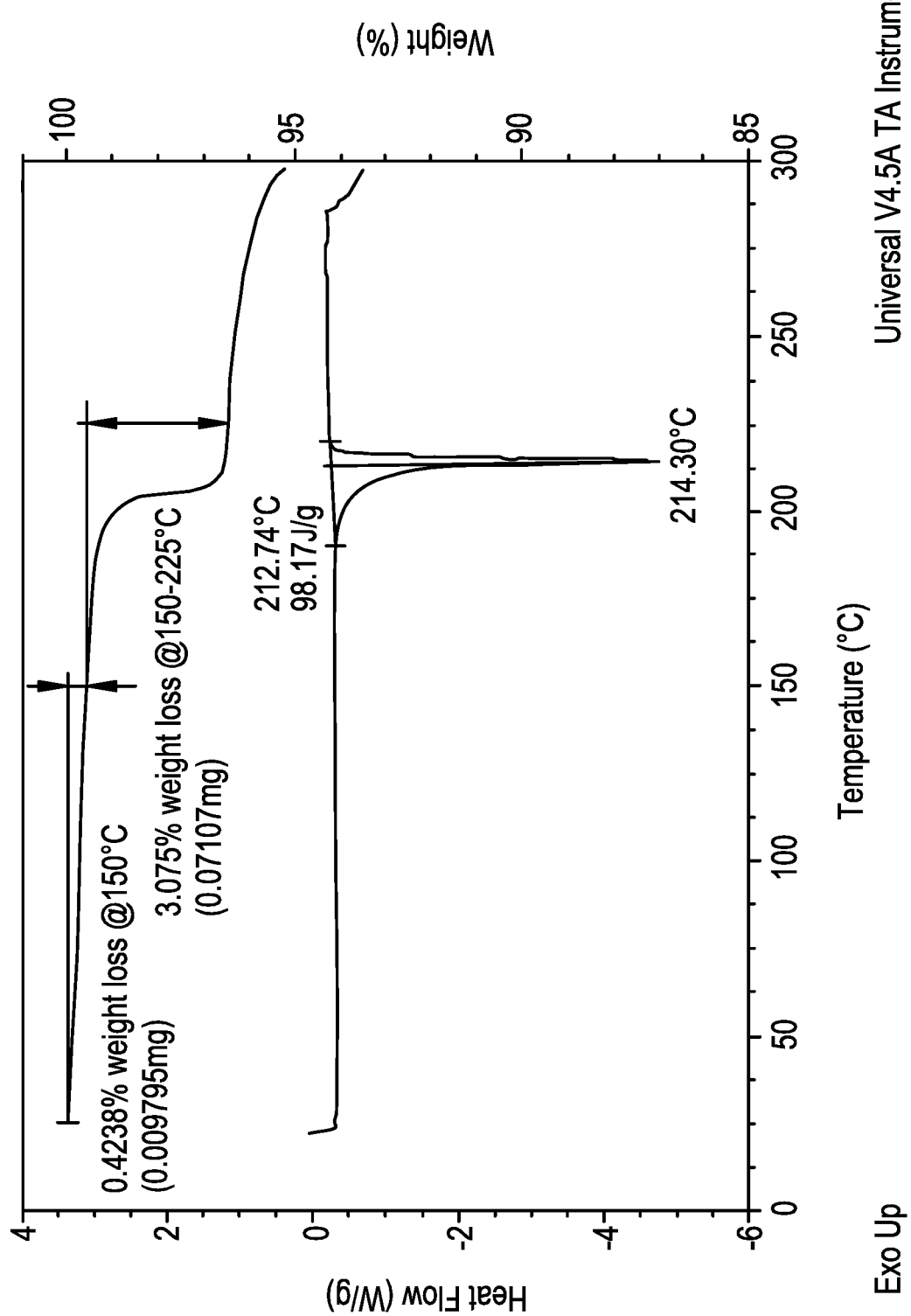
FIG. 3 illustrates the differential scanning calorimetry (DSC) and thermogravimetric analysis (TGA) traces of (S)-2-amino-N-((3R,5R)-8-hydroxy-6-oxo-7-oxa-1-aza-8-boraspiro[4.7]dodecan-3-yl)-3-methylbutanamide Form D.

Example 1 was analyzed by thermal techniques. DSC analysis indicated that Form D had an endotherm event of dehydrate with an onset at about 213° C. and a peak at about 214° C. TGA indicated that Example 1 exhibited a mass loss of about 0.4% upon heating from about 25° C. to about 150° C. and a mass loss of about 3.1% upon heating from about 150° C. to about 225° C. A representative DSC/TGA thermogram of Example 1 is shown in FIG. 3.

Figure 4:
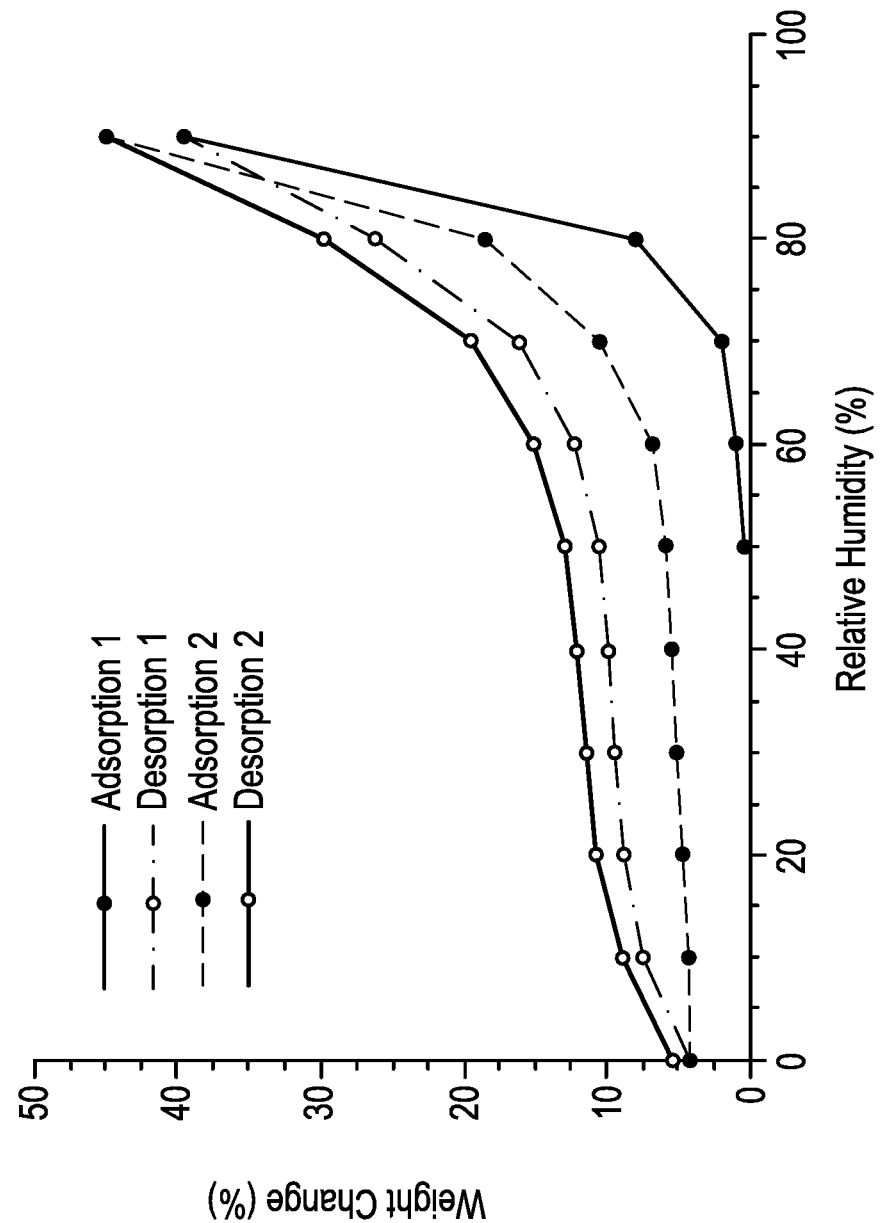
FIG. 4 illustrates the gravity vapor sorption (GVS) traces of (S)-2-amino-N-((3R,5R)-8-hydroxy-6-oxo-7-oxa-1-aza-8-boraspiro[4.7]dodecan-3-yl)-3-methylbutanamide Form D.

Example 1 was analyzed by gravity vapor sorption. GVS analysis indicated that Example 1 absorbed less than 2% water at the relative humidity (RH) of 70% and started to deliquesce after 80% RH. A representative GVS thermogram of Example 1 is shown in FIG. 4.

Example 2: (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1 (the acetone adduct) Form 1

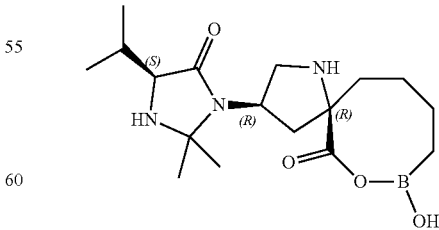

An amount of 20.3 mg of Intermediate 9 was suspended in 2.0 ml of acetone. The solid was dissolved after 200 µl of $H_2O$ was added. The solvent was removed by evaporation in the ambient condition. The resulting solid was suspended in 1.0 ml of acetone and stirred at the ambient temperature for 3 days. After the solvent was dried in air, crystalline material (rod-like crystals) of the acetone adduct was obtained and designated as (3R,5R)-8-hydroxy-3-((S)-4-isopropyl-2,2-dimethyl-5-oxoimidazolidin-1-yl)-7-oxa-1-aza-8-boraspiro[4.7]dodecan-6-one.

Figure 5:
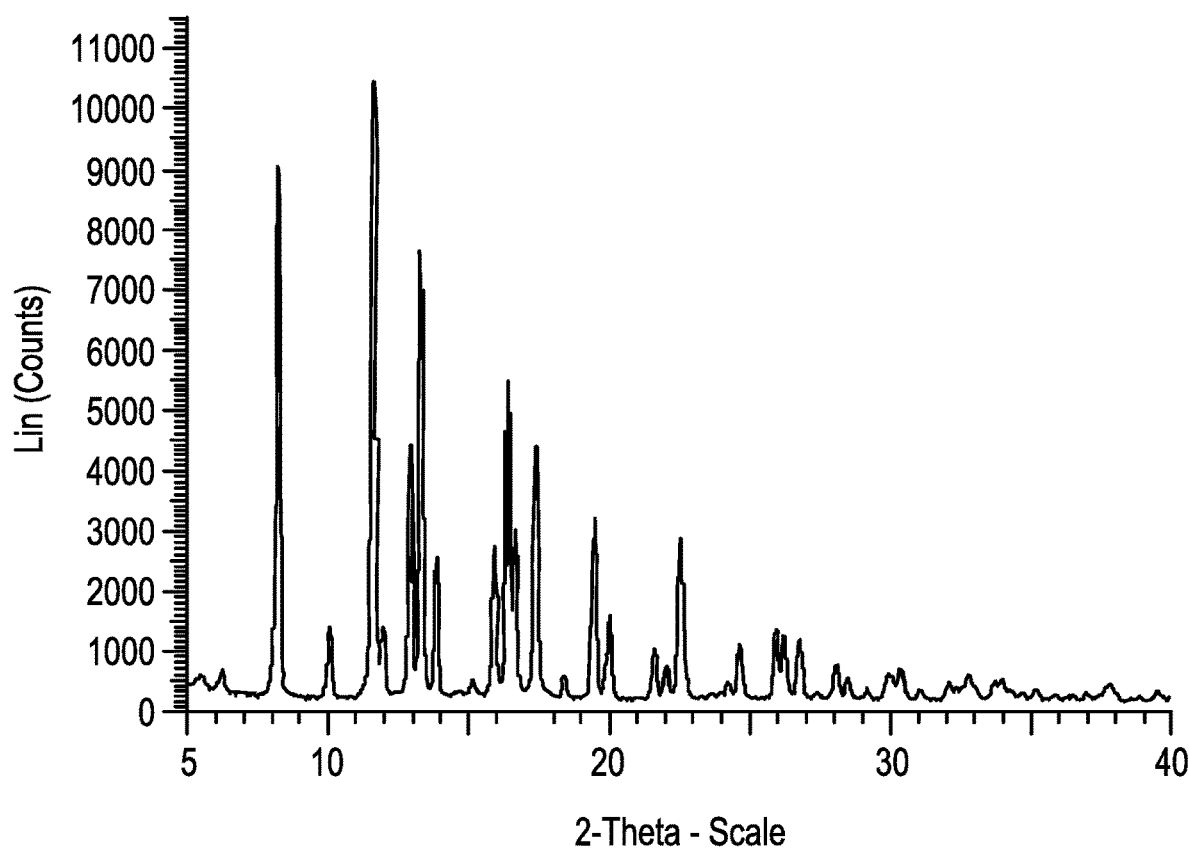
FIG. 5 illustrates the powder X-ray diffraction diagram of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1.

Example 2 was analyzed by XRPD and the results are tabulated below (Table 2) and shown in FIG. 5.

TABLE 2

XRPD Peaks for the acetone adduct

| Angle (2θ ± 0.2°) | Intensity (%) |
|---|---|
| 11.6 | 100.0 |
| 8.2 | 84.7 |
| 13.3 | 70.0 |
| 16.4 | 52.3 |
| 12.9 | 41.7 |
| 17.4 | 41.2 |
| 19.5 | 29.6 |
| 16.6 | 28.5 |
| 22.6 | 27.4 |
| 15.9 | 27.3 |

Example 2 was characterized in providing at least one of the following 2θ±0.2° values measured using CuKα radiation: 11.6, 8.2, and 13.3°.

Figure 6:
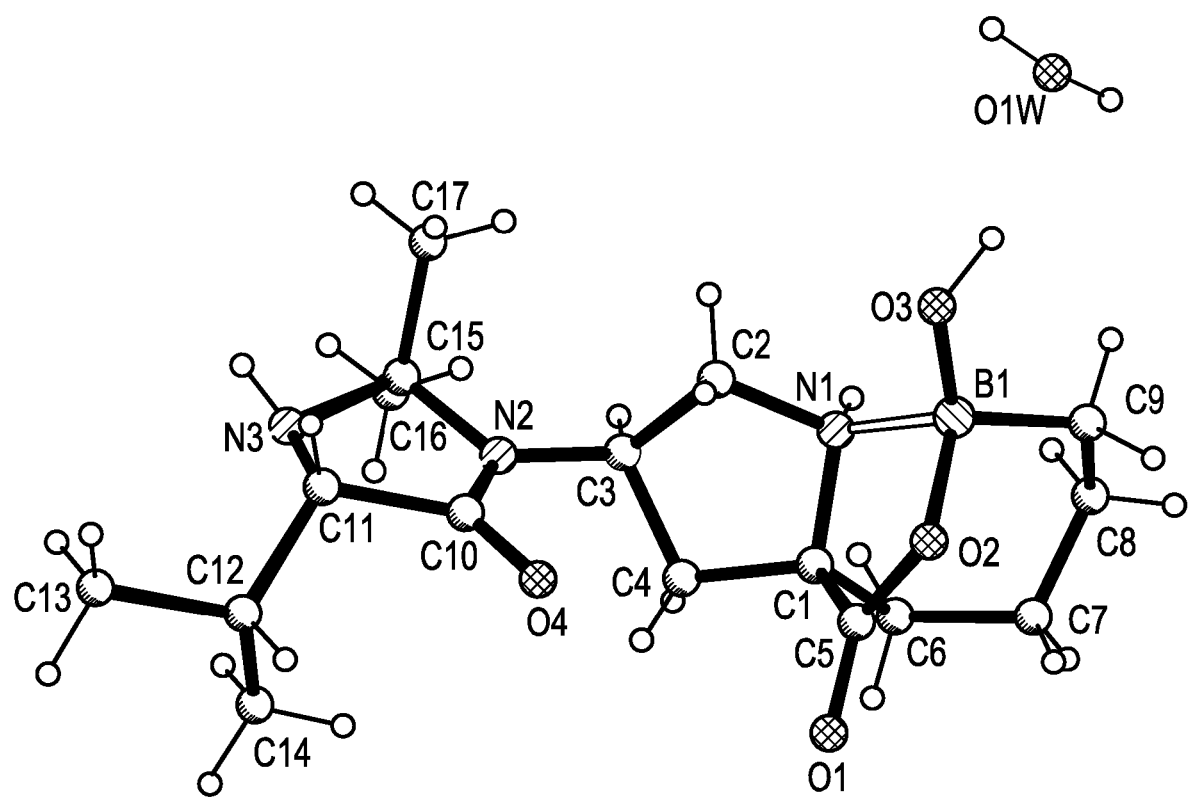
FIG. 6 illustrates the single crystal structure of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1.

Single crystals of Example 2 were obtained from slow evaporation of an acetone/H2O solution. Single crystal structure analysis confirmed that the acetone is a monohydrate. The molecular structure of the acetone adduct is shown in FIG. 6. Crystallographic data: Space group orthorhombic $P2_12_12_1$, unit cell dimensions: a=8.4752(8) Å, b=13.7561(14) Å, c=17.6681(16) Å, V=2059.8(3) Å$^3$.

Example 2 was analyzed by thermal techniques. DSC analysis indicated that the acetone adduct had an endotherm event of dehydrate with an onset at 82° C. and a peak at 122° C. Another endotherm event of dehydrate was also identified with an onset at 177° C. and a peak at 182° C.

Figure 7:
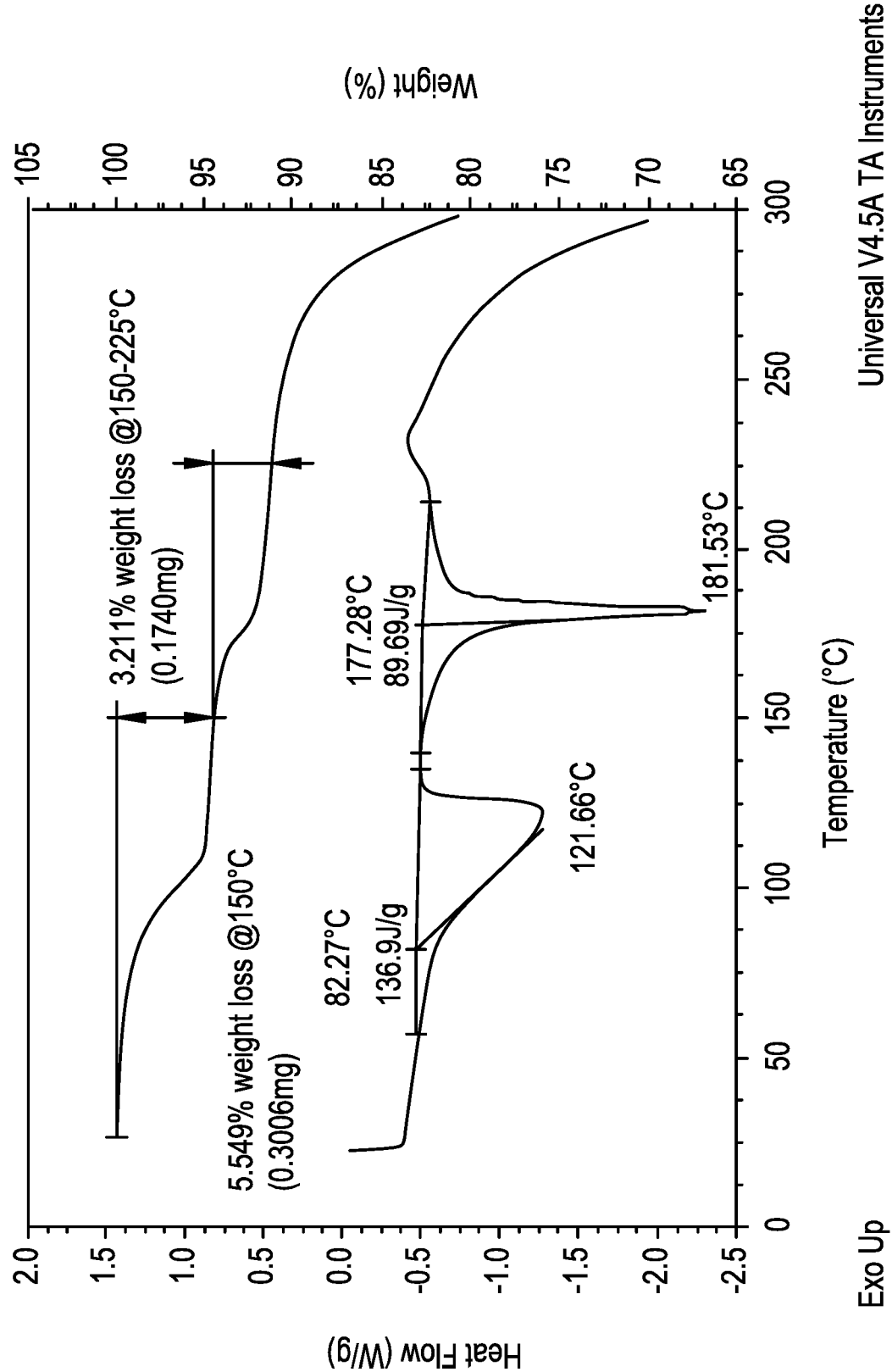
FIG. 7 illustrates the differential scanning calorimetry (DSC) and thermogravimetric analysis (TGA) traces of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1.

TGA indicated that the acetone adduct exhibits a mass loss of about 5.5% upon heating from about 25° C. to about 150° C. and a mass loss of about 3.2% upon heating from about 150° C. to about 225° C. A representative DSC/TGA thermogram of the acetone is shown in FIG. 7.

Figure 8:
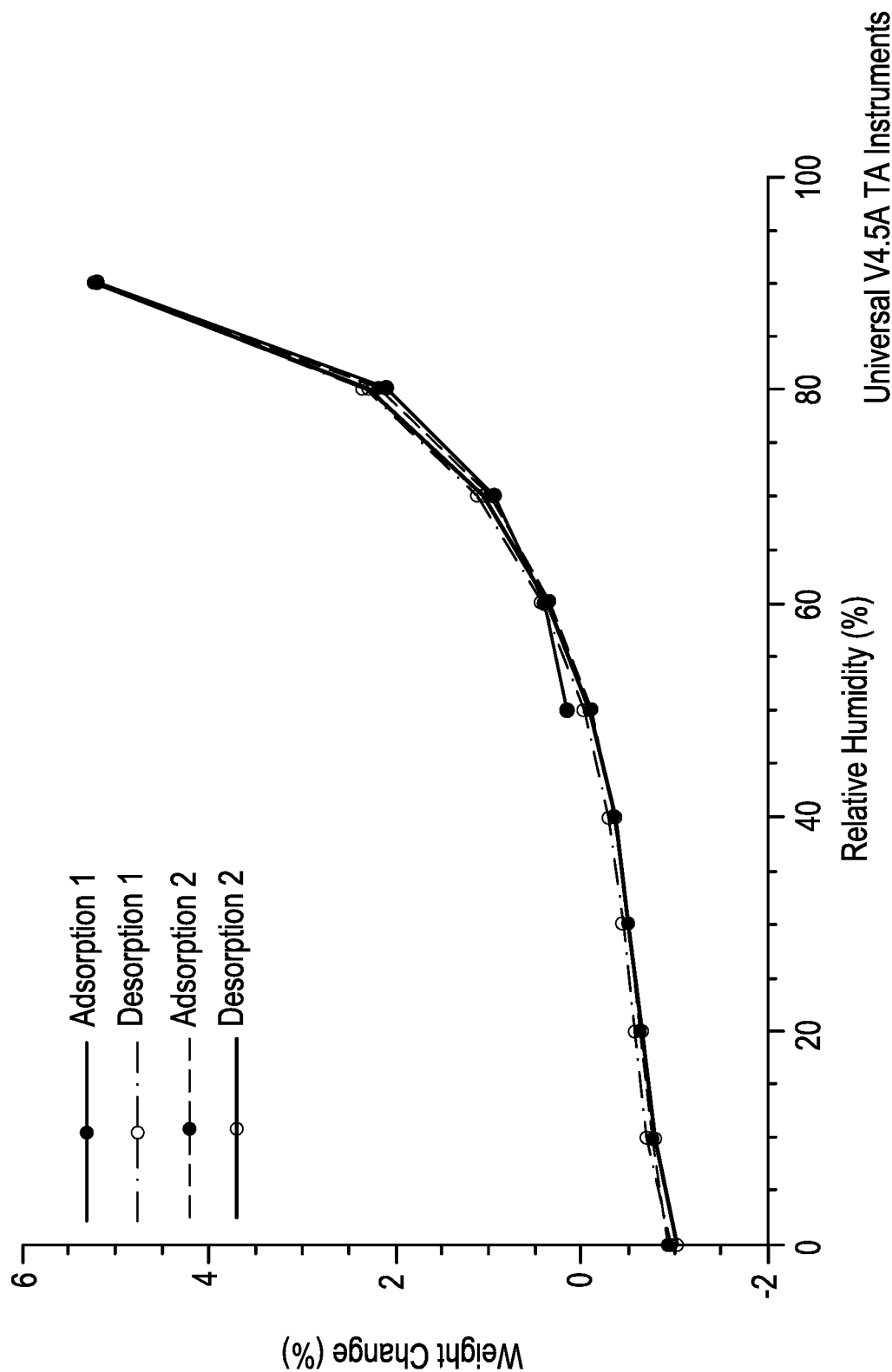
FIG. 8 illustrates the gravity vapor sorption (GVS) traces of (3R,5R)-8-hydroxy-3-((S)-4-isopropyl-2,2-dimethyl-5-oxoimidazolidin-1-yl)-7-oxa-1-aza-8-boraspiro[4.7]dodecan-6-one Form 1.

Example 2 was analyzed by gravity vapor sorption. GVS analysis indicated that the acetone adduct absorbs less than 2% water at the relative humidity (RH) of 80%. A representative GVS thermogram of acetone adduct is shown in FIG. 8.

Example 3: (S)-2-amino-N-((3R,5R)-8-hydroxy-6-oxo-7-oxa-1-aza-8-boraspiro[4.7]dodecan-3-yl)-3-methylbutanamide Form E An amount of 30 mg of Intermediate 9 was suspended in 0.50 mL of ethyl acetate, previously saturated with water. The suspension was heated to 75° C. and stirred at 75° C. for 1 hour. The suspension was then cooled down to the ambient temperature and the solid was filtered and dried in air. Crystalline material with needle/rod crystals was obtained and designated as (S)-2-amino-N-((3R,5R)-8-hydroxy-6-oxo-7-oxa-1-aza-8-boraspiro[4.7]dodecan-3-yl)-3-methylbutanamide Form E.

Figure 9:
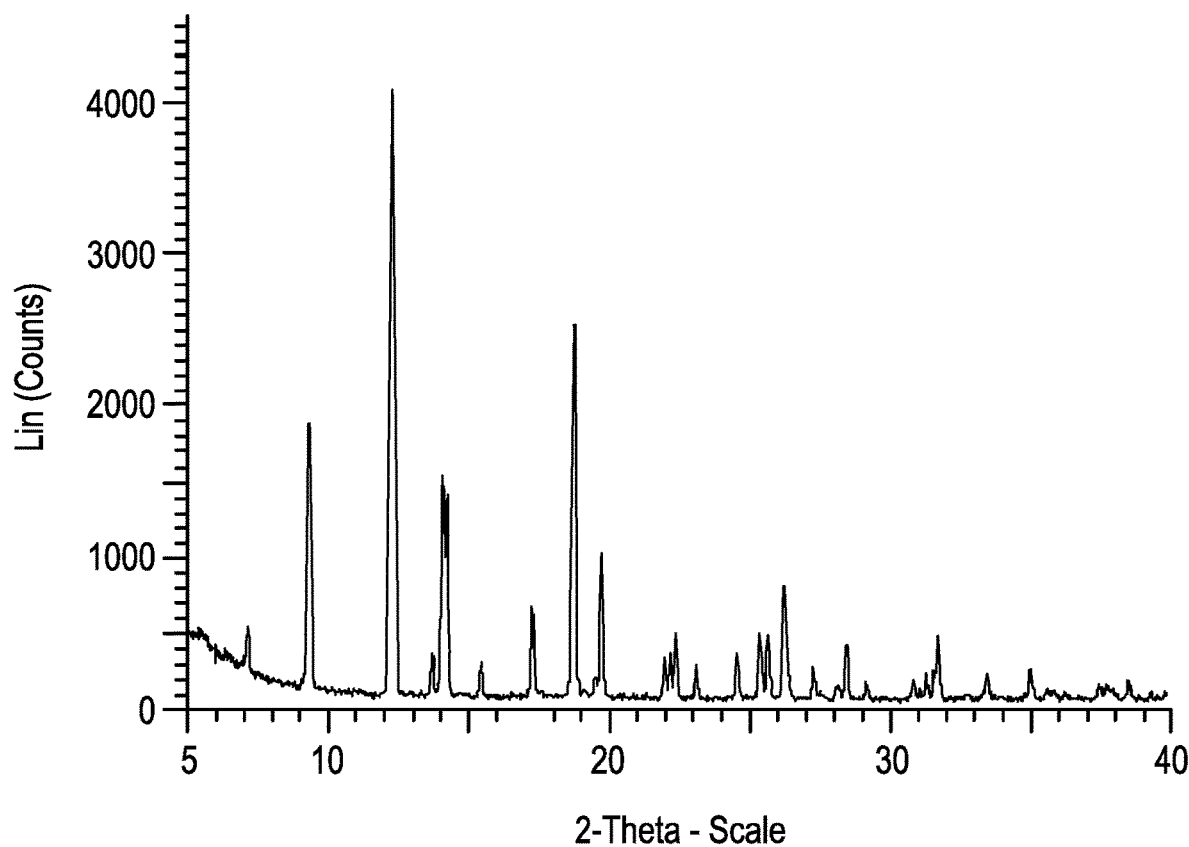
FIG. 9 illustrates the powder X-ray diffraction diagram of (S)-2-amino-N-((3R,5R)-8-hydroxy-6-oxo-7-oxa-1-aza-8-boraspiro[4.7]dodecan-3-yl)-3-methylbutanamide Form E.

Example 3 was analyzed by XRPD and the results are tabulated below (Table 3) and shown in FIG. 9.

TABLE 3

XRPD Peaks for Form E

| Angle (2θ ± 0.2°) | Intensity (%) |
|---|---|
| 12.3 | 100.0 |
| 18.8 | 64.1 |
| 9.3 | 46.9 |
| 14.2 | 35.9 |
| 14.1 | 35.2 |
| 19.8 | 26.1 |
| 26.2 | 19.5 |
| 17.3 | 17.5 |
| 7.1 | 14.0 |
| 25.4 | 13.4 |

Example 3 was characterized in providing at least one of the following 2θ±0.2° values measured using CuKα radiation: 12.3, 18.8, and 9.3°.

Figure 10:
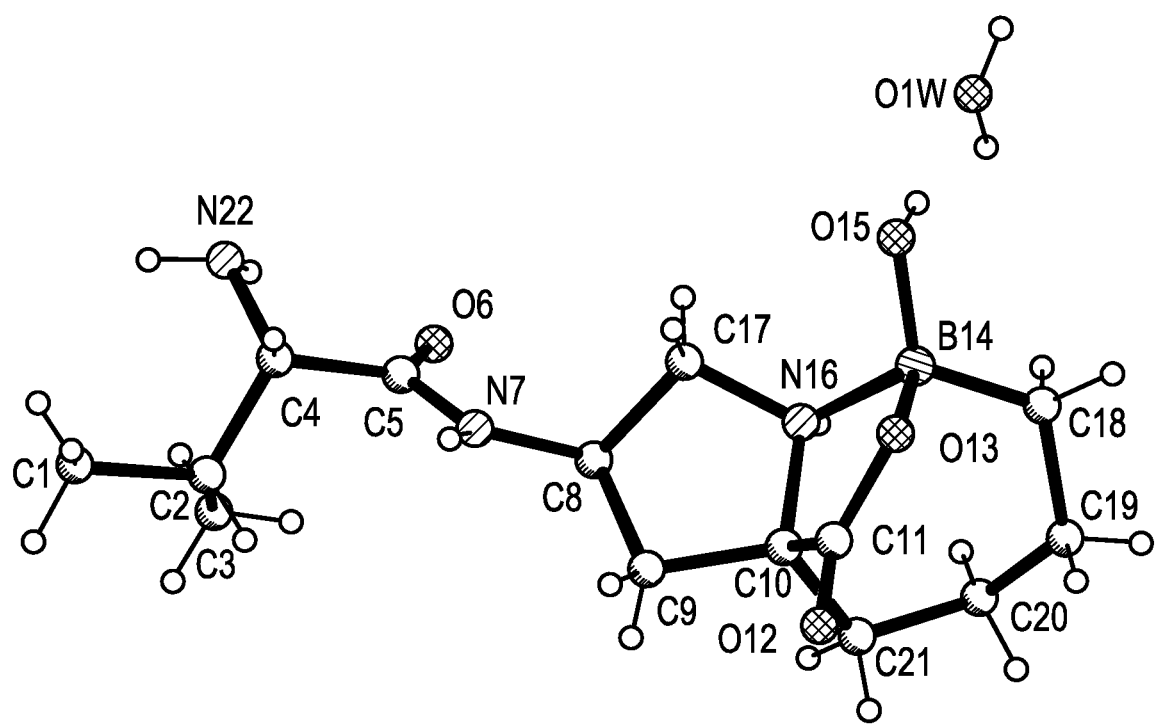
FIG. 10 illustrates the single crystal structure of (S)-2-amino-N-((3R,5R)-8-hydroxy-6-oxo-7-oxa-1-aza-8-boraspiro[4.7]dodecan-3-yl)-3-methylbutanamide Form E.

Single crystals of Example 3 were obtained from slow evaporation of the clear solution with a mixture solvent of acetonitrile/water (ratio 20:1) and single crystal structure analysis confirmed that Example 3 is a monohydrate form. The molecular structure of Example 3 is shown in FIG. 10. Crystallographic data: Space group hexagonal $P6_1$, unit cell dimensions: a=14.4509(4) Å, b=14.4509(4) Å, c=14.6815(10) Å, V=2655.2(2) Å$^3$.

Figure 11:
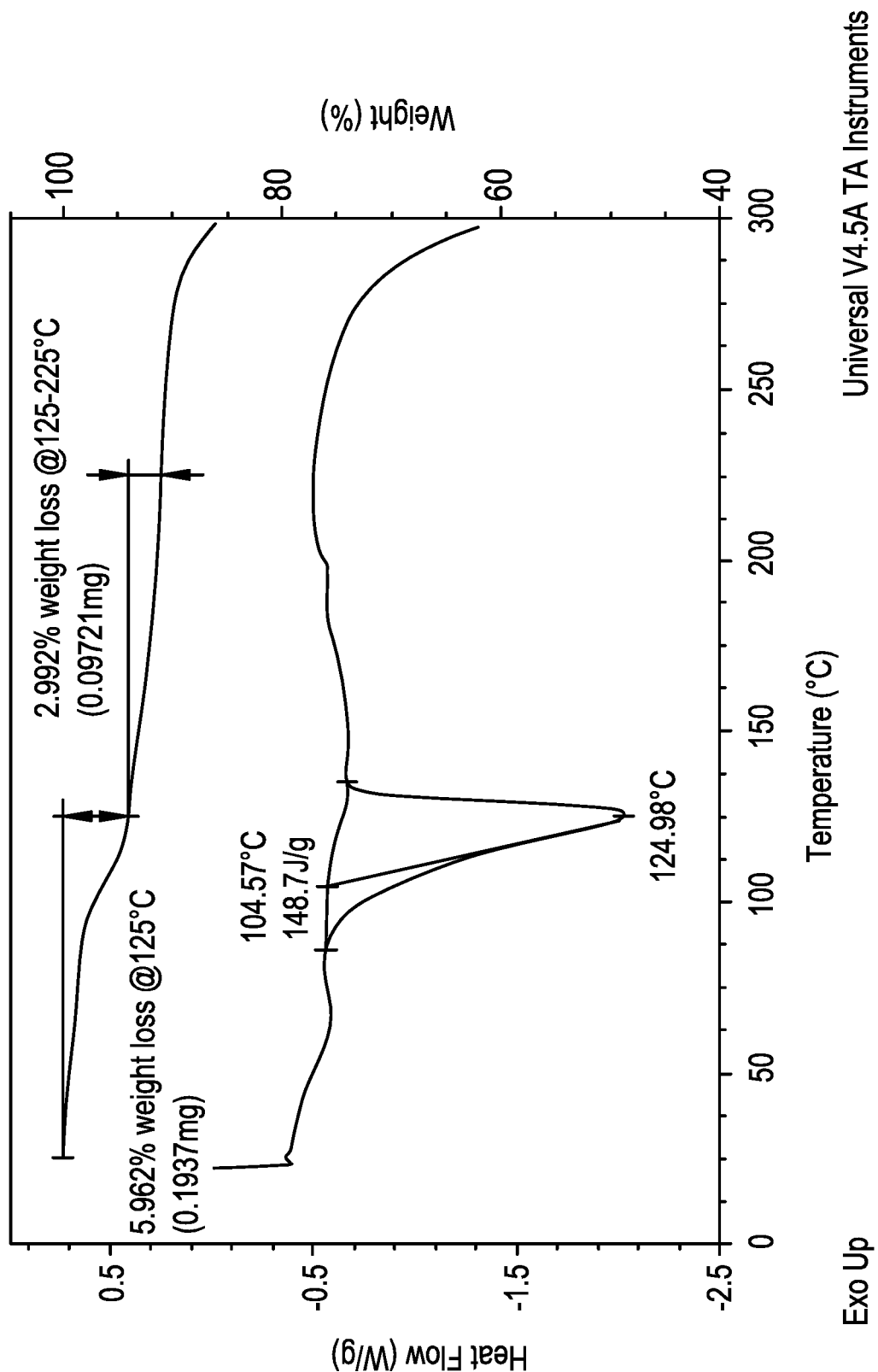
FIG. 11 illustrates the differential scanning calorimetry (DSC) and thermogravimetric analysis (TGA) traces of (S)-2-amino-N-((3R,5R)-8-hydroxy-6-oxo-7-oxa-1-aza-8-boraspiro[4.7]dodecan-3-yl)-3-methylbutanamide Form E.

Example 3 was analyzed by thermal techniques. DSC analysis indicated that Form E had an endotherm event of dehydrate with an onset at about 105° C. and a peak at about 125° C. Another endotherm event of dehydrate was also identified with a broad range between about 125° C. to about 225° C. TGA indicated that Example 3 exhibits a mass loss of about 6.0% upon heating from about 25° C. to about 135° C. and a mass loss of about 3.0% upon heating from about 125° C. to about 225° C. A representative DSC/TGA thermogram of the acetone is shown in FIG. 11.

Example 3 was analyzed by gravity vapor sorption. GVS analysis indicated that Example 3 absorbed less than 2% water at the relative humidity (RH) of 80%. A representative GVS thermogram of Example 3 is shown in FIG. 12.

Example 4: Biological Activity

Crystalline materials Form D (Example 1), Form 1 (Example 2) and Form E (Example 3) convert to the same active chemical moiety when dissolved in an aqueous medium, e.g., at the physiological condition. The inhibitory effects of Example 1 on the activity of Human Arginase 1 and Arginase 2 activity were quantified by measuring the formation of the thiol group from thioarginine using recombinant Arginase 1 or Arginase 2 produced from *E. coli*. The thiol group was detected with Ellman's reagent, 5,5'-dithiobis(2-nitrobenzoic acid) (DTNB). DTNB reacts with the thiol to give the mixed disulfide and 2-nitro-5-thiobenzoic acid (TNB) which is quantified by the absorbance of the anion (TNB$^{2-}$) at 412 nm.

The assays were run in clear 384 well plates (Greiner cat no: 781101). Various concentrations of Example 1 in 300 nL DMSO were dispensed to assay plates using an Echo acoustic dispenser immediately followed by plate sealing and centrifugation.

Two pre-mixes were prepared from reagents thawed immediately before addition to assay plates. Pre-mix one comprised human Arginase 1 or human Arginase 2, at a final concentration of 5 nM and 0.5 mM DTNB in assay buffer, 45 mM HEPES pH7.5, brij 35, 0.045% (w/v) and 100 μM MnCl$_2$. Pre-mix two comprised freshly thawed 0.5 mM thioarginine in assay buffer. Fifteen microlitres of pre-mix one was dispensed to assay plates containing Example 1, centrifuged and incubated for 30 minutes at room temperature prior to adding fifteen microlitres of pre-mix two.

Assay plates were centrifuged prior to reading absorbance at 412 nm in a Pherastar multi-mode plate reader to collect data at time point 0 (T0). The plates were incubated at room temperature for 60 min prior to reading again to collect data at time point 1 (T1). Data is derived by subtracting the A412 signal measured at T0 (time point 0) from that measured at T1 (time point 1). The data was transformed to % effect using the equation:

$$\text{Compound \% effect} = 100 * [(X - \text{min})/(\text{max} - \text{min})],$$

where X represents the normalized value for the compound based on the Min (vehicle) and Max (reference compound) inhibition control.

The concentration of Example 1 that inhibited the activity by 50% (i.e., the $IC_{50}$) was calculated by plotting the % effect versus test compound concentration and fitting the data using the Genedata Screener Smart fit algorithm. The $IC_{50}$ of Example 1 for Arginase 1 was 0.222 µM and 0.282 for Arginase 2.

The invention claimed is:

1. A crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprising peaks with the following values: 7.8, 19.2, and 15.0 degree 2θ±0.2°.

2. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 1, wherein the X-ray powder diffraction pattern further comprises peaks at 16.4, 13.1, and 13.7 degree 2θ±0.2°.

3. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 2, wherein the X-ray powder diffraction pattern is as shown in FIG. 1.

4. The crystalline (S)-2-amino-N-((3R,5R)-8-hydroxy-6-oxo-7-oxa-1-aza-8-boraspiro[4.7]dodecan-3-yl)-3-methylbutanamide Form D characterized by an X-ray powder diffraction pattern comprising at least 3 peaks selected from 7.8, 19.2, 15.0, 16.4, 13.1, 13.7, 26.4, 19.8, 17.9, and 22.5 degree 2θ±0.2°.

5. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 4, characterized by an X-ray powder diffraction pattern comprising at least 5 peaks selected from 7.8, 19.2, 15.0, 16.4, 13.1, 13.7, 26.4, 19.8, 17.9, and 22.5 degree 2θ±0.2°.

6. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 1, further characterized by a differential scanning calorimetry (DSC) curve that comprises an endotherm at about 214° C.

7. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 6, wherein the DSC curve is as shown in FIG. 3.

8. A pharmaceutical composition comprising crystalline (S)-2-amino-N-((3R,5R)-8-hydroxy-6-oxo-7-oxa-1-aza-8-boraspiro[4.7]dodecan-3-yl)-3-methylbutanamide Form D according to claim 1 and a pharmaceutically acceptable carrier.

9. A pharmaceutical composition comprising an effective amount of (S)-2-amino-N-((3R,5R)-8-hydroxy-6-oxo-7-oxa-1-aza-8-boraspiro[4.7]dodecan-3-yl)-3-methylbutanamide according to claim 1 and a pharmaceutically acceptable carrier, wherein at least about 85%, or at least about 90%, or at least about 95%, or at least about 96%, or at least about 97%, or at least about 98%, or at least about 99%, or at least about 99.5% of (S)-2-amino-N-((3R,5R)-8-hydroxy-6-oxo-7-oxa-1-aza-8-boraspiro[4.7]dodecan-3-yl)-3-methylbutanamide is in Form D.

10. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form D according to claim 1.

11. A crystalline (S)-2-amino-N-((3R,5R)-8-hydroxy-6-oxo-7-oxa-1-aza-8-boraspiro[4.7]dodecan-3-yl)-3-methylbutanamide Form E characterized by an X-ray powder diffraction pattern comprising peaks with the following values: 12.3, 18.8, and 9.3 degree 2θ±0.2°.

12. A pharmaceutical composition comprising crystalline (S)-2-amino-N-((3R,5R)-8-hydroxy-6-oxo-7-oxa-1-aza-8-boraspiro[4.7]dodecan-3-yl)-3-methylbutanamide Form E according to claim 11 and a pharmaceutically acceptable carrier.

13. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form E according to claim 11.

14. A pharmaceutical composition comprising crystalline (S)-2-amino-N-((3R,5R)-8-hydroxy-6-oxo-7-oxa-1-aza-8-boraspiro[4.7]dodecan-3-yl)-3-methylbutanamide Form D according to claim 4 and a pharmaceutically acceptable carrier.

15. A pharmaceutical composition comprising an effective amount of (S)-2-amino-N-((3R,5R)-8-hydroxy-6-oxo-7-oxa-1-aza-8-boraspiro[4.7]dodecan-3-yl)-3-methylbutanamide according to claim 4 and a pharmaceutically acceptable carrier, wherein at least about 85%, or at least about 90%, or at least about 95%, or at least about 96%, or at least about 97%, or at least about 98%, or at least about 99%, or at least about 99.5% of (S)-2-amino-N-((3R,5R)-8-hydroxy-6-oxo-7-oxa-1-aza-8-boraspiro[4.7]dodecan-3-yl)-3-methylbutanamide is in Form D.

16. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form D according to claim 4.

17. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 1, wherein a dative bond is formed between the nitrogen atom of the pyrrolidine moiety and the boron atom, as represented by an arrowed line in the following structural formula:

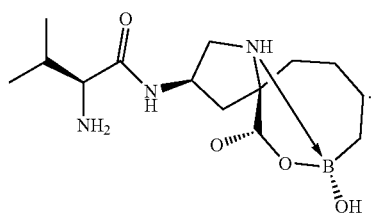 [SMILES: CC(C)[C@H](N)C(=O)N[C@H]1C[NH+]2[B@@-]3(O)CCCC[C@@]2(C1)[C@@H](O)O3]

18. A pharmaceutical composition comprising crystalline (S)-2-amino-N-((3R,5R)-8-hydroxy-6-oxo-7-oxa-1-aza-8-bora spiro[4.7] dodecan-3-yl)-3-methylbutanamide Form D according to claim 17 and a pharmaceutically acceptable carrier.

19. A pharmaceutical composition comprising an effective amount of (S)-2-amino-N-((3R,5R)-8-hydroxy-6-oxo-7-oxa-1-aza-8-boraspiro[4.7]dodecan-3-yl)-3-methylbutanamide according to claim 17 and a pharmaceutically acceptable carrier, wherein at least about 85%, or at least about 90%, or at least about 95%, or at least about 96%, or at least about 97%, or at least about 98%, or at least about 99%, or at least about 99.5% of (S)-2-amino-N-((3R,5R)-8-hydroxy-6-oxo-7-oxa-1-aza-8-boraspiro[4.7]dodecan-3-yl)-3-methylbutanamide is in Form D.

20. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form D according to claim 17.

21. The crystalline (S)-2-amino-N-((3R,5R)-8-hydroxy-6-oxo-7-oxa-1-aza-8-boraspiro[4.7]dodecan-3-yl)-3-methylbutanamide Form D according to claim 4, wherein a dative bond is formed between the nitrogen atom of the pyrrolidine moiety and the boron atom, as represented by an arrowed line in the following structural formula:

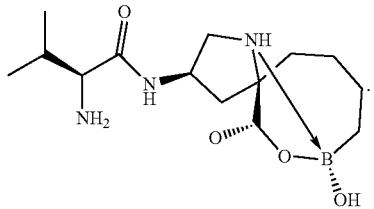 [SMILES: CC(C)[C@H](N)C(=O)N[C@H]1C[NH+]2[B@@-]3(O)CCCC[C@@]2(C1)[C@@H](O)O3]

22. A pharmaceutical composition comprising crystalline (S)-2-amino-N-((3R,5R)-8-hydroxy-6-oxo-7-oxa-1-aza-8-bora spiro[4.7] dodecan-3-yl)-3-methylbutanamide Form D according to claim 21 and a pharmaceutically acceptable carrier.

23. A pharmaceutical composition comprising an effective amount of (S)-2-amino-N-((3R,5R)-8-hydroxy-6-oxo-7-oxa-1-aza-8-boraspiro[4.7]dodecan-3-yl)-3-methylbutanamide according to claim 21 and a pharmaceutically acceptable carrier, wherein at least about 85%, or at least about 90%, or at least about 95%, or at least about 96%, or at least about 97%, or at least about 98%, or at least about 99%, or at least about 99.5% of (S)-2-amino-N-((3R,5R)-8-hydroxy-6-oxo-7-oxa-1-aza-8-boraspiro[4.7]dodecan-3-yl)-3-methylbutanamide is in Form D.

24. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form D according to claim 21.

25. The crystalline (S)-2-amino-N-((3R,5R)-8-hydroxy-6-oxo-7-oxa-1-aza-8-boraspiro[4.7]dodecan-3-yl)-3-methylbutanamide Form E according to claim 11, wherein a dative bond is formed between the nitrogen atom of the pyrrolidine moiety and the boron atom, as represented by an arrowed line in the following structural formula:

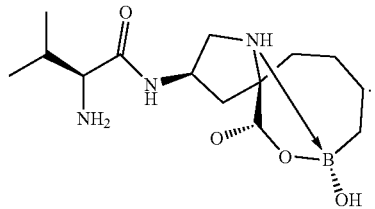 [SMILES: CC(C)[C@H](N)C(=O)N[C@H]1C[NH+]2[B@@-]3(O)CCCC[C@@]2(C1)[C@@H](O)O3]

26. A pharmaceutical composition comprising crystalline (S)-2-amino-N-((3R,5R)-8-hydroxy-6-oxo-7-oxa-1-aza-8-boraspiro[4.7] dodecan-3-yl)-3-methylbutanamide Form E according to claim 25 and a pharmaceutically acceptable carrier.

27. A method of treating cancer associated with arginase 1 and/or arginase 2 modulation comprising administering to a subject an effective amount of crystalline ((S)-2-amino-N-((3R,5R)-8-hydroxy-6-oxo-7-oxa-1-aza-8-boraspiro[4.7]dodecan-3-yl)-3-methylbutanamide Form E according to claim 25.

* * * * *